(12) United States Patent
Ozeki et al.

(10) Patent No.: US 7,132,072 B2
(45) Date of Patent: Nov. 7, 2006

(54) METHOD FOR PRODUCING MULTI-CORED MOLDED ARTICLE

(75) Inventors: Yuichi Ozeki, Nagoya (JP); Yoshiya Kondo, Nagoya (JP); Yukinao Watanabe, Nagoya (JP)

(73) Assignee: Sanwa Kagaku Kenkyusho Co., Ltd., Nagoya (JP)

( * ) Notice: Subject to any disclaimer, the term of this patent is extended or adjusted under 35 U.S.C. 154(b) by 105 days.

(21) Appl. No.: 10/490,880

(22) PCT Filed: Sep. 24, 2002

(86) PCT No.: PCT/JP02/09808

§ 371 (c)(1),
(2), (4) Date: Aug. 13, 2004

(87) PCT Pub. No.: WO03/026560

PCT Pub. Date: Apr. 3, 2003

(65) Prior Publication Data

US 2005/0013960 A1    Jan. 20, 2005

(30) Foreign Application Priority Data

Sep. 26, 2001 (JP) ............................ 2001-292682

(51) Int. Cl.
*B29C 43/04* (2006.01)
(52) U.S. Cl. .................. 264/113; 264/120; 425/344; 425/345; 425/352; 425/353; 425/354
(58) Field of Classification Search ............... None
See application file for complete search history.

(56) References Cited

U.S. PATENT DOCUMENTS

| | | | | |
|---|---|---|---|---|
| 4,419,413 A | * | 12/1983 | Ebihara | ............... 428/548 |
| 4,996,014 A | * | 2/1991 | Suvanto | ............... 264/113 |
| 5,088,915 A | * | 2/1992 | Korsch et al. | ............... 425/345 |
| 5,221,503 A | * | 6/1993 | Ward et al. | ............... 264/104 |
| 2005/0202082 A1 | * | 9/2005 | Hibino et al. | ............... 424/464 |

FOREIGN PATENT DOCUMENTS

| | | | |
|---|---|---|---|
| DE | 829022 | * | 12/1952 |
| DE | 2834226 | * | 2/1980 |
| GB | 743222 | * | 1/1956 |
| GB | 1034713 | * | 6/1966 |

(Continued)

*Primary Examiner*—Mary Lynn Theisen
(74) *Attorney, Agent, or Firm*—Michael L. Crapenhoft

(57) ABSTRACT

To manufacture a multi-core press-coated molded product efficiently and in a single step from molding materials, namely, powder or granular particles, a punch has been devised that is characterized in that the punch, consists of a center punch whose tip portion is split into two or more parts, and an outer punch enclosing the outer perimeter of the center punch, and whose tip portion fills the gap at the tip portion of the center punch, with both the center and outer punches being slidable and manipulatable for compression operation the method of manufacturing a multi-core press-coated molded product using the punch of the invention as compression molding means for at least the upper punch and preferably for both the upper and lower punches, and a rotary compression molding machine therefore is also discribed. This has led to the successful manufacture of a multi-core press-coated molded product in which a plurality of cores are arranged horizontally relative to the pressure applied surface of the molded product and further located at specific positions. When provided with a score line, the multi-core press-coated molded product can be made into a dividable molded product.

6 Claims, 12 Drawing Sheets

FOREIGN PATENT DOCUMENTS

| | | | |
|---|---|---|---|
| JP | 52-126577 | | 10/1977 |
| JP | 55-048653 | | 4/1980 |
| JP | 58-116187 | | 8/1983 |
| JP | 61-001610 | * | 1/1986 |
| JP | 61-060298 | | 3/1986 |
| JP | 62-114907 | | 5/1987 |
| JP | 01-273698 | | 11/1989 |
| JP | 02-243157 | | 9/1990 |
| JP | 02-243158 | | 9/1990 |
| JP | 09-206358 | | 8/1997 |
| JP | 2000-061699 | | 2/2000 |
| JP | 2001-072579 | | 3/2001 |
| JP | 2002-065812 | | 3/2002 |
| WO | WO 03/018302 | | 6/2003 |

* cited by examiner (A)

(B)

METHOD FOR PRODUCING MULTI-CORED MOLDED ARTICLE

TECHNICAL FIELD

The present invention relates generally to a molded product manufactured by compressing bulk materials in the form of powder or granular particles, etc. that are molding materials, as well as to a manufacturing method thereof and an apparatus used therefor, and, more particularly, to a molded product having a plurality of cores (multi-core press-coated molded product), a manufacturing method thereof and punches and rotary compression molding machine for use therein.

BACKGROUND ART

Rotary compression molding machines called rotary tabletting machines are often used to manufacture molded products by compressing a powder or granular particles in the fields of pharmaceuticals, foods, electronic components and so on. Among such molded products, those which have a core inside are used in the field of drugs and are called press-coated tablets due to the fact that a powder or granular particles serving as an outer layer is compression-molded outside a core tablet (center tablet).

SUMMARY

Press-coated tablets having a core tablet therein ensure reduced probability of contact between core and outer layer ingredients, holding promise for improved stability as a result of reduced interaction between ingredients. Further, they are used to mask the bitter taste or improve the aesthetics of the core tablet. Such tablets are also used in controlled release formulations having ingredients with different elution properties in the core and the outer layer and so on. Thus, covering the core tablet containing drug ingredients with powder or granular particles or film ingredients is widely used for the various reasons given above.

On the other hand, administration of a half tablet in which a tablet is divided has recently come into wide use to address pharmacokinetic changes undergone by individual patients from the viewpoint of patients' QOL (Quality of Life). However, if the outer layer containing the core tablet is a controlled release coating (e.g., enteric coating, sustained release coating), administration of a divided tablet may result in the drug not delivering its inherent properties or causing side effects, thus making drug splitting impossible at present. Further, press-coated or film-coated tablet containing optically unstable drug ingredients results, if split, in ready exposure of the core tablet to the outside environment, making administration of a divided tablet problematic for the aforementioned reasons.

Next, the conventional art of tabletting for press-coated tablets will be described. A description will be given of the conventional art of a molded product having a single core (single-core press-coated molded product) first, followed by a description of a molded product having a plurality of cores (multi-core press-coated molded product).

When a single-core press-coated molded product is manufactured, the core is prepared in advance as a molded product by a separate tabletting machine, and then the core or molded product is further supplied into the die of the tabletting machine for press-coated tablets, followed by supply of powder or granular particles for the outer layer and compression molding. For this reason, the workload is considerably higher than with manufacturing methods for ordinary compression molded products, leading to a major problem—low productivity. In the conventional method of supplying molded products or cores, on the other hand, such molded products or cores are each supplied individually into the die within the fast rotating turntable, frequently resulting in cores not being supplied or too many thereof supplied into the die and therefore producing molded products with no or too many cores. To prevent such problems, complicated mechanisms/devices are required to monitor core supply and inspect final products for quality assurance purposes, giving rise to larger and more complex machines.

Further, it is essential to place the core level at the center portion of the powder or granular particles for the outer layer during compression molding in the conventional core supply method. Displacement of the core from the center results in the outer layer of that area becoming thinner, making products prone to molding failures such as capping—peeling of part of the molded body—and lamination—cracking of the molded product in layered form.

To prevent core-centering error due to centrifugal force on the turntable, a visual core centering inspection method following core supply is described in Japanese Patent Application Laid-Open Publication No. 55-48653. Japanese Patent Application Laid-Open Publication No. 61-60298 describes an apparatus, provided with a multi-optical axes color code sensor, that functions in a coordinated fashion with a core supply device to automatically rectify the core position. Further, a method is described in Japanese Patent Application Laid-Open Publication No. 9-206358 of preventing core centering error by an apparatus that automatically corrects the core supply position based on information obtained from a CCD imaging device.

However, it is normally difficult to operate even the aforementioned core centering apparatus with a high-speed turntable (40 to 60 rpm), which are ordinarily used in tabletting machines, due to problems including core centering accuracy and stable core supply, To be used effectively, the operation speed of the turntable must be limited to up to 30 rpm or so. This obviously results in low production efficiency.

As for the size of molded products containing a core, the conventional method requires at least 1 to 1.5 mm for the outer layer thickness due to variations in core centering, naturally resulting in core-containing molded products as a whole being sized at least 2 to 3 mm larger than the core. Therefore, core-containing molded products tend to be larger than coreless molded products, constituting a bottleneck for downsizing of molded products.

As for the core shape, the conventional method of supplying cores from outside requires designing of a dedicated supply device tailored to the core shape. For this reason, when a molded product is manufactured using cores of various shapes, various core supply devices are needed, leaving the problem of lack of versatility unsolved.

Moreover, the conventional method supplies cores prepared in advance, requiring the cores with moldability enough to withstand transport along the supply path into the die and shaped so as to ensure smooth transport, as a result of which there exists a number of limitations in relation to the core shape and physical properties. That is, it is absolutely impossible for the conventional method to manufacture a molded product containing a core not molded in solid form or containing a powder or granular particles itself as core.

While molded products containing a single core face the aforementioned status quo and involve the problems as described above, there exists no substantial conventional art for molded products containing a plurality of cores because a rotary tabletting machine capable of processing such cores is nonexistent in the industry at present.

As far as the literature is concerned, a method is described of downsizing press-coated tablets by introducing a plurality of small-sized core tablets into the die in Japanese Examined Patent Application Publication No. 5-65187. However, the described method leaves the aforementioned state of the art and problems associated with single-core press-coated molded products unsolved. Besides, the method requires a large number of cores to be manufactured in advance for introduction of a plurality of cores. This leads to significantly reduced production efficiency as compared with conventional single-core press-coated tablets, requiring a several fold higher cost and time than ordinary tablets and thus making this method a nonviable option hardly industrially. Moreover, addition of the step for introducing core tablets will inevitably complicate the core supply mechanism. The consequence is not only more the frequent occurrence of products with no or too many cores but also new problems such as inconsistent positions of a plurality of cores and different core positions from one molded product to another, for example, due to interference between cores within the die.

Further, if a plurality of small-sized cores are introduced into an oddly shaped molded product (e.g., football-shaped, track field-shaped), it is more difficult to maintain gaps between the cores and the outer layer surface (particularly at the tip portion on the side along the length) than when core tablets are introduced into a round molded product, making it necessary, when a plurality of large cores are introduced, to arrange the cores adjacent to each other at the center of the oddly shaped molded product. Conversely, to arrange cores at the tip portion along the length in consideration of possible scoring, the core tablets must be reduced to an extremely small size or the tablet itself must be upsized. Moreover, the aforementioned problem will manifest itself of how to ensure consistency in positions of a plurality of cores such that the cores are arranged at specific positions.

Next, the conventional art for double punch will be described.

In actual compression molding using a compression molding apparatus, a powder or granular particles supplied into the die is pressed using punches so as to sandwich the powder or granular particles from above and below for molding. Depending on the shape of the molded product manufactured, punches of various shapes are used and, under certain circumstances, special punches are needed. For example, a molded product in troche form with a hollowed center used in the field of drugs involves difficulties in charging a powder or granular particles uniformly with normal punches. Since hollowing of the center is required in addition to the above, compression molding of such a molded product is carried out using a double punch, or so-called ring punch.

In manufacturing molded products in a complicated shape used for wide-ranging applications, including electronic components, a molded product may arise whose powder or granular particles density is considerably different from one part of the product to another the product due to differences in the compression ratio attributed to its complicated shape. This may lead to cracking or chipping in the molded product cracking or chipping. To solve these problems, therefore, a method is used of charging a powder or granular particles so as to ensure identical density of powder or granular particles within the molded product by employing a multiple punch having a structure similar to that of the ring punch in the lower punch mechanism of the rotary powder compression molding machine described in Japanese Patent Application Laid-Open Publication No. 52-126577 and by moving the lower center and outer punches separately. However, such conventional double-structured punches called ring punches are employed, for example, to aid in charging powder or granular particles or secure a ring-shaped hollow, and are therefore often used only for the lower punch, with the center punch thereof being fixed in most cases.

As set forth hereinabove, splitting a press-coated molded product has hitherto constituted a problem out of a fear of impairing the properties of ingredients within the cores. Besides, manufacturing a press-coated molded product has made it inevitable to confront problems including productivity, cost, occurrences of molded products with no or too many cores, displacement of cores due to centrifugal force of the turntable, molding failures arising therefrom and limitations in relation to core shape. Further, producing a multi-core press-coated molded product has involved various problems including more frequent occurrences of molded products with no or too many cores, position uniformity of a plurality of cores and upsizing of final molded product. To solve all these problems at once, it suffices to mold a molded product having a plurality of cores in a single step using powder or granular particles as raw materials instead of supplying a plurality of cores molded in advance in solid form. Therefore, the present inventors have perfected, based on the aforementioned idea, the present invention with an object of providing a press-coated molded product capable, under certain circumstances, of being split, a manufacturing method thereof and an apparatus therefor in a realistically usable form.

To solve the aforementioned object, the present inventors have devised a punch, characterized in that the punch consists of a center punch whose tip portion is split into two or more parts and an outer punch enclosing the outer perimeter of the center punch and whose tip portion fills the gap at the tip portion of the center punch, with both the center and outer punches being slidable and manipulatable for compression operation, and a method of manufacturing a multi-core press-coated molded product using compression molding means that use the present punch at least for the upper punch and preferably for both the upper and lower punches. The method of manufacturing a multi-core press-coated molded product includes supply steps respectively for powder or granular particles for the cores and the outer layer, compression molding steps for the powder or granular particles for the cores and/or the outer layer and a compression molding step for the entire molded product. One embodiment of the method is a method of manufacturing a multi-core press-coated molded product that includes an outer layer supply step 1 in which a powder or granular particles for the outer later is supplied into spaces enclosed by a lower outer punch and above a lower center punch, a core supply step in which a powder or granular particles for the cores is supplied into spaces enclosed by the lower outer punch and above the powder or granular particles for the outer layer supplied in the previous step, an outer layer/core molding step in which the powder or granular particles for the outer layer and the cores supplied by the time of the previous step are compression-molded, an outer layer supply step 2 in which a powder or granular particles for the outer layer is further supplied into a space above and around the molded products of the outer layer and the core in the die molded in the previous step, and an overall molding step in which the molded products of the outer layer and the core and the powder or granular particles for the outer layer are compression-molded. An alternative embodiment is a method of manufacturing a multi-core press-coated molded product that includes an outer layer supply step 1 in which a powder or granular particles for the outer later is supplied into a space enclosed by the die and above the lower punch, an outer layer molding step in which the supplied powder or granular particles for the outer layer is compression-molded into a pot shape by the upper and lower punches with the upper center punch projecting toward the lower center punch, a core supply step in which a powder or granular particles for the cores is supplied into spaces within the pot-shaped molded product of the outer layer, an outer layer supply step 2 in which a powder or granular particles for the outer layer is further supplied into a space above the molded product of the outer layer or powder or granular particles for the cores within the die that has been supplied or supplied and molded by the time of the previous step, and an overall molding step in which molded product of the outer layer or powder or granular particles for the cores and the powder or granular particles for the outer layer are compression-molded.

In the present invention, an apparatus has been conceived for manufacturing a multi-core press-coated molded product as apparatus for carrying out the manufacturing method. The apparatus being a rotary compression molding machine characterized in having a rotatable turntable provided with a die having a die hole and performing compression operation of powder or granular particles charged into the die by holding upper and lower punches above and below the die so as to be vertically slidable, moving the upper and lower punches in mutually approaching directions and pressing the powder or granular particles with the punch tips left inserted in the die. The apparatus using, for at least the upper punch and preferably for both the upper and lower punches, a punch consisting of a center punch whose tip portion is split into two or more parts and an outer punch enclosing the outer perimeter of the center punch and whose tip portion fills the gap at the tip portion of the center punch, with both the center and outer punches being slidable and manipulatable for compression operation, and the apparatus comprising means for moving the center and outer punches of the punch and means for allowing manipulation of the center and outer punches for compression operation and the apparatus being provided, on the same turntable, with supply portions respectively for powder or granular particles for the cores and the outer layer, compression molding portions for the powder or granular particles for the cores and/or the outer layer, and a compression molding portion for the entire multi-core press-coated molded product. That is, the present manufacturing apparatus is a rotary compression molding machine constructed so as to perform a series of steps of the method of manufacturing a multi-core press-coated molded product of the present invention.

As a result, a multi-core press-coated molded product having an outer layer and a plurality of cores therein was successfully manufactured using the present invention, with the plurality of cores arranged horizontally relative to the pressure applied surface of the molded product. The present invention is also characterized in being capable of arranging a plurality of cores at specific positions and provides a mass of multi-core press-coated molded products characterized in a plurality of cores being arranged at specific positions. It is also possible, under certain circumstances, that the present invention may provide a dividable multi-core press-coated molded product with a score line on the outer layer surface or a mass thereof.

BRIEF DESCRIPTION OF THE DRAWINGS

FIG. 2(A) illustrates a vertical side view (right side) and a side view (left side), FIG. 2(B) a top view, and FIG. 2(C) a vertical sectional perspective view;

FIG. 3(A) illustrates a vertical sectional view (right half) and a schematic view (left half), FIG. 3(B) a side view, and FIG. 3(C) a view of a punch tip, with the double punch corresponding to FIG. 7;

FIG. 8(A) illustrates a bird's-eye view, and FIG. 8(B) a top view;

DETAILED DESCRIPTION

Figure 1:
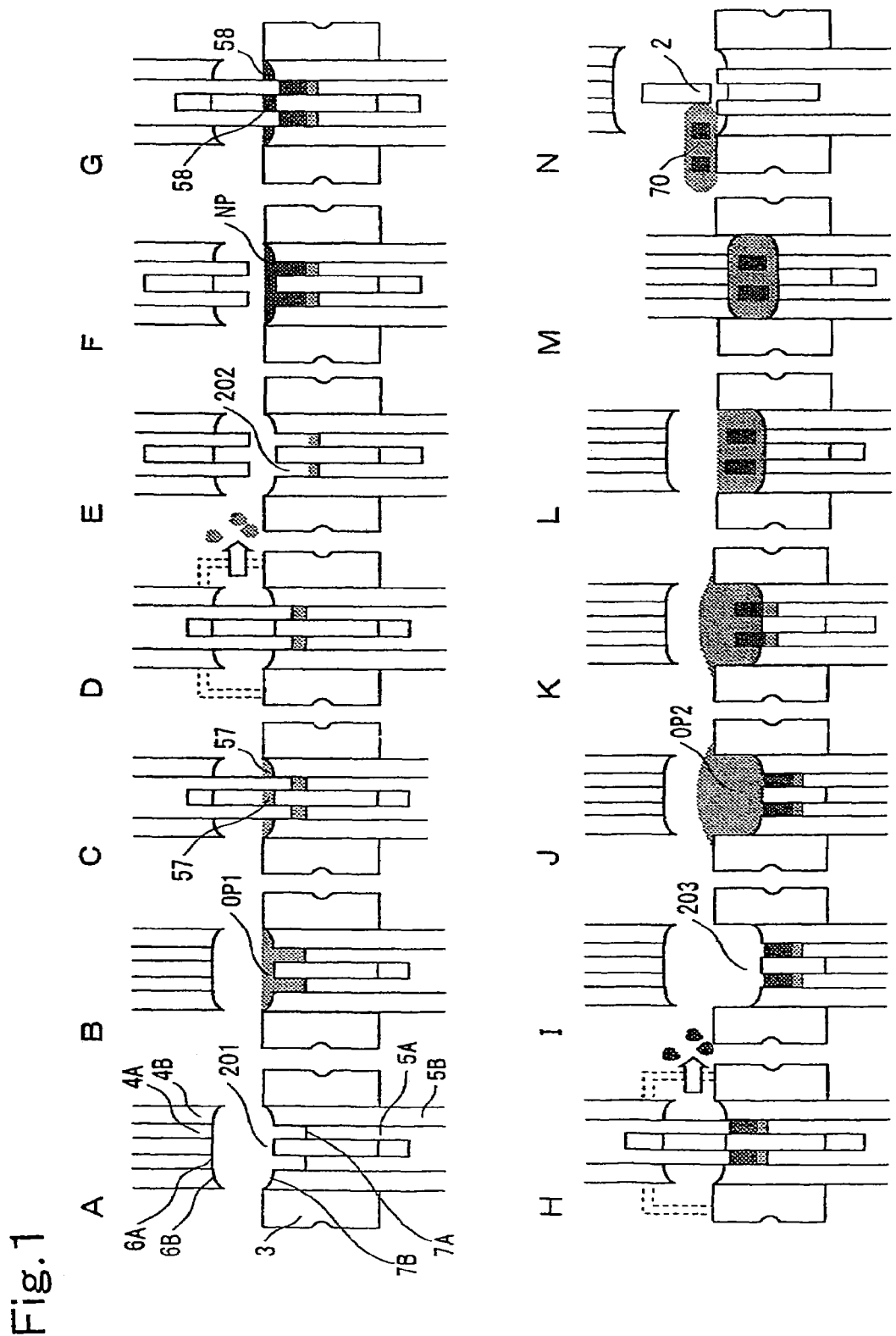
FIG. 1 illustrates explanatory views of punch tip operations showing a first example of a manufacturing method of a multi-core press-coated molded product of the present invention (shading as cross section omitted)

The multi-core press-coated molded product of the present invention is characterized in that the molded product has an outer layer and a plurality of cores therein that are arranged horizontally relative to the pressure applied surface of the molded product and that the outer layer and the cores are integrally molded.

Here, the term "pressure applied surface of the molded product" refers to the surface, perpendicular to the direction in which pressure is applied by the punches during compression molding, that is expected to receive pressure. "Horizontal direction relative to the pressure applied surface of the molded product" is synonymous with vertical direction relative to the pressure applied surface of the molded product. The term "integral molding" refers to compression molding through a series of steps by using only a set of punches and die. The term has a meaning in contrast with conventional press-coated molded products manufactured by molding a core in advance and supplying it in the middle of molding step.

On the other hand, the term "a plurality of cores" refers to two or more cores, and while there are normally only two to several cores, cores may be increased to the extent that the punch can be manufactured. That is, in the case of a large-sized punch, the tip portion of the center punch can be split into a large number of parts, making it possible to produce a multi-core press-coated molded product containing many cores.

The multi-core press-coated molded product of the present invention is further characterized in that a plurality of cores can be arranged at specific positions. While the conventional manufacturing method could manufacture multi-core press-coated molded products, core positions varied from one product to another, making it impossible to mass-produce a multi-core press-coated molded product in which the core positions among a plurality of cores, could be maintained. In other words, a plurality of cores could not be arranged at specific positions. Therefore, the multi-core press-coated molded product of the present invention can be worded as a "mass of multi-core press-coated molded products characterized in that its usefulness becomes apparent when grasped as a mass of many and that cores are arranged at consistent specific positions." Here, the term "mass" conveys a meaning of a number of molded products mass-produced by a single molding machine and a set of punches and die and may, more specifically, be 100 pieces or more, or 1000 pieces or more, or 10000 pieces or more. On the other hand, arrangement of a plurality of cores at specific positions allows for the outer layer thickness to be reduced to the utmost limit, thus making possible further downsizing of molded products.

The size and shape of the multi-core press-coated molded product of the present invention are not specifically limited as long as the punch can be manufactured. The same holds true for the inner core size, and the inner core may, depending on the tip shape of the center punch, take on various shapes. Further, the sizes of individual cores need not be the same.

One embodiment of the multi-core press-coated molded product of the present invention is a dividable multi-core press-coated molded product or a mass thereof characterized in having an outer layer with a score line on the surface and a plurality of cores therein, with the plurality of cores arranged horizontally relative to the pressure applied surface of the molded product. Here, it is preferred that there exists a plurality of cores in respective portions separated by surfaces divided by score lines. As for the number of cores, two cores are generally the most common, and in this case the two cores are arranged separately on the right and left sides of a single score line on the outer layer surface. Alternatively, it is possible to divide a molded product unevenly depending on the shape of the score line. In the case of a dividable molded product, while the shape of the molded product is not specifically limited, it is preferred that the molded product be basically an oblong shape in consideration of ease of score. It is to be understood that the preferred shape of molded products varies depending on the number of scores and the purpose of use. For example, when a two-core dividable molded product is evenly divided, it is preferred that the molded product be oddly shaped such as football-shaped or capsule-shaped molded product. On the other hand, when a four-core dividable molded product is evenly divided, it is preferred that the molded product be round from the viewpoint of its size and strength.

It is also possible for the multi-core press-coated molded product of the present invention to constitute the inner cores mainly by moldability-poor ingredients and unevenly distribute ingredients excellent in moldability in the outer layer. For instance, active ingredients in drugs are normally low in moldability and therefore not molded alone. The present invention, however, substantially allows for only active ingredients to be contained in the cores (contained ingredients: lubricant, anti-agglutinator or so) and ingredients excellent in moldability to be contained only in the outer layer. This makes it possible to produce a small-sized and highly moldable multi-core press-coated molded product and further provide improved stability to those ingredients whose activity drops as a result of diluting effect.

A description will be given next of the manufacturing method and apparatus of the multi-core press-coated molded product of the present invention.

In the present specification, the term "powder or granular particles" is intended to encompass all molding materials including powders and granules, except where the term "powder" is particularly commonly used.

The present invention employs a punch (punch of the present invention) consisting of a center punch whose tip portion is split into two or more parts and an outer punch enclosing the outer perimeter of the center punch and whose tip portion fills the gap at the tip portion of the center punch, with both the center and outer punches being slidable and manipulatable for compression operation. The method of manufacturing the multi-core press-coated molded product of the present invention employs compression molding means having punches above and below a die, with the punch of the present invention used for at least the upper punch and preferably for both the upper and lower punches. The method of manufacturing the multi-core press-coated molded product of the present invention includes supply steps respectively for powder or granular particles for the cores and the outer layer and compression molding steps for the powder or granular particles for the cores and/or the outer layer, and an overall molding step for the entire multi-core press-coated molded product. It is to be noted that the supply steps are used in a broad sense and may be called supply/charging steps. The supply step for powder or granular particles for the outer layer is normally performed at least twice.

More specifically, such steps are an outer layer supply step 1 in which a powder or granular particles for the outer later is supplied into spaces enclosed by a lower outer punch and above a lower center punch, a core supply step in which a powder or granular particles for cores is supplied into spaces enclosed by the lower outer punch and above the powder or granular particles for the outer layer supplied in the previous step, an outer layer/core molding step in which the powder or granular particles for the outer layer and the cores supplied by the time of the previous step are compression-molded, an outer layer supply step 2 in which a powder or granular particles for the outer layer is further supplied into a space above and around the molded products of the outer layer and the core in the die molded in the previous step, and an overall molding step in which the molded products of the outer layer and the core and the powder or granular particles for the outer layer are compression-molded. It is possible to add other steps to the present manufacturing method as necessary. Here, the term "powder or granular particles for the outer layer" as in "space above the powder or granular particles for the outer layer", needless to say, includes a molded product of the outer layer.

If ordinary powder or granular particles are used in the method of manufacturing the multi-core press-coated molded product of the present invention of the embodiment, it is preferred that an outer layer molding step, in which the powder or granular particles for the outer layer is compression-molded, be carried out immediately after the outer layer supply step 1. This of prevents contamination between the powder or granular particles for the outer layer and the cores and making a clear distinction between outer layer and core portions.

It is also preferred in the present method that temporary compression be carried out as the compression operation in an outer layer/core molding step and the outer layer molding step described above. A molded product made in this case can be called temporary molded product. While the main compression may be performed as the compression operation in the overall molding step, it is preferred that precompression (temporary compression) be carried out first followed by main compression. Thus, temporary compression is designed to enhance integrality of eventually produced molded products and allow for downsizing of finished molded products.

It is also possible to manufacture a multi-core press-coated molded product with a plurality of cores further existing in plurality and continuously along the direction in which pressure is applied to the molded product by repeating the core supply step or both the core supply and outer layer/core molding steps of the present invention. In this case, it is possible, by further using a powder or granular particles for the cores as powder or granular particles to be supplied after use of a powder or granular particles for the outer layer in the repetitive steps, to manufacture a multi-core press-coated molded product, with a powder or granular particles for the outer layer sandwiched between cores that are aligned along the direction in which pressure is applied to the molded product. It is also possible to use a powder or granular particles different from that used for the first core as powder or granular particles supplied in the repetitive steps.

Depending on the shape of the punch tip, it is further necessary in the method of manufacturing the multi-core press-coated molded product of the present invention to perform a step of removing any residual powder or granular particles remaining on the lower outer punch and/or the molded product. However, this step may be optional. A detailed description thereof will be given later.

Among other embodiments of the manufacturing method are a method of manufacturing a multi-core press-coated molded product that includes an outer layer supply step 1 in which a powder or granular particles for the outer later is supplied into a space enclosed by the die and above the lower punch, an outer layer molding step in which the supplied powder or granular particles for the outer layer is compression-molded into a pot shape by the upper and lower punches with the upper center punch projecting toward the lower punch, a core supply step in which a powder or granular particles for cores is supplied into spaces within the pot-shaped molded product of the outer layer, an outer layer supply step 2 in which a powder or granular particles for an outer layer is further supplied into a space above the molded product of the outer layer or powder or granular particles for the cores within the die that has been supplied or supplied and molded by the time of the previous step, and an overall molding step in which the molded product of the outer layer or powder or granular particles for the cores and the powder or granular particles for the outer layer are compression-molded. The present method is preferred when microcapsule or controlled release granules (granule having enteric coating, sustained release coating and such) extremely poor in core moldability are used as powder or granular particles for the cores which are supplied into pot-shaped spaces in the pot-shaped molded product of the outer layer. Unlike the aforementioned manufacturing method, outer layer compression molding operation is essential following the outer layer supply step 1 in the present method out of the need to manufacture the pot-shaped molded product of the outer layer. It is to be noted that the outer layer/core molding step is carried out, as necessary after the core supply step, in which the powder or granular particles for the cores or the powder or granular particles for the cores and the molded product of the outer layer are compression-molded.

The pot-shaped molded product of the outer layer in the present manufacturing method can be molded by directly pressing the powder or granular particles for the outer layer supplied into a space enclosed by the die and above the lower punch, with the upper center punch projecting toward the lower punch. That is, the molding process of can be performed without any problem using an ordinary punch for the lower punch when the cores are small in quality and the recesses in the pot-shaped molded product are small. If, however, the recesses in the pot-shaped molded product are large, powder or granular particles charging is slightly more problematic. The cause lies in that the powder or granular particles charged in planar form is formed into a recessed portion by the projecting upper center punch alone, thus resulting in insufficient charging of the powder or granular particles onto the side. To ensure uniform charging, for this reason, the present problem can be resolved by projecting the lower center punch in advance and then charging the powder or granular particles. That is, it suffices to charge the powder or granular particles after moving the lower center punch so as to ensure a lesser amount of powder or granular particles is charged at the portion corresponding to the recesses in the pot-shaped molded product.

It is necessary in the present embodiment, as in the manufacturing method of the aforementioned embodiment, to perform a step of removing residual powder or granular particles primarily remaining on the molded product, or it may be preferred to do so.

A detailed description will be given below of a first example of the method of manufacturing the multi-core press-coated molded product of the present invention mainly with reference to FIG. 1. It is to be understood here that the outer layer molding step is performed and that temporary compression operation is used.

First, with a lower center punch 5A lowered (FIG. 1A), a powder or granular particles for the first outer layer OP1 is supplied into first outer layer spaces 201 enclosed by a lower outer punch 5B and above the lower center punch 5A (FIG. 1B). After raising the lower center punch 5A as necessary and thus removing the excess powder or granular particles for the first outer layer OP1 from the die, an upper center punch 4A and the lower center punch 5A are moved to engage each other for temporary compression (FIG. 1C), thus temporarily molding the first outer layer.

Next, with the temporary molded products of the first outer layer OP1 held by the lower center and outer punches 5A and 5B, a powder or granular particles for cores NP is supplied into core spaces 202 enclosed by the lower outer punch 5B and above the temporary molded products of the first outer layer OP1 by lowering the lower center punch 5A as necessary (FIG. 1F). Then, after raising the lower center punch 5A as necessary and thus removing the excess powder or granular particles for the cores from the die, the upper and lower center punches 4A and 5A are moved to engage each other for temporary compression (FIG. 1G), thus temporarily molding the temporary molded product of the first outer layer and the core.

Further, with the temporary molded products of the first outer layer and the core held by the lower center and outer punches 5A and 5B, the powder or granular particles for a second outer layer OP2 is supplied into a second outer layer space 203 above and around the temporary molded products of the first outer layer and the core within a die 3 (FIG. 1J) by lowering the lower punch (both the lower center and outer punches 5A and 5B or the lower outer punch 5B) (FIG. 1I). The temporary molded products of the core held on the temporary molded products of the first outer layer are allowed to be completely covered with the powder or granular particles for the outer layer and the temporary molded products of the outer layer (FIGS. 1K to 1L), and the excess powder or granular particles for the second outer layer OP2 is removed as necessary out of the die 3 (FIG. 1L). It should be noted that the powder or granular particles for the second outer layer OP2 can be supplied after sufficiently lowering the lower outer punch 5B first such that the temporary molded products of the first outer layer and the core are apparently pushed up. Then, the upper punch (both the upper center and outer punches 4A and 4B) and the lower punch (both the lower center and outer punches 5A and 5B) are moved to engage each other for precompression (temporary compression) of the entire molded product consisting of the first outer layers, the cores and the second outer layer as necessary, eventually followed by main compression (FIG. 1M). The step shown in FIG. 1N is for ejecting the completed molded product.

Figure 2:
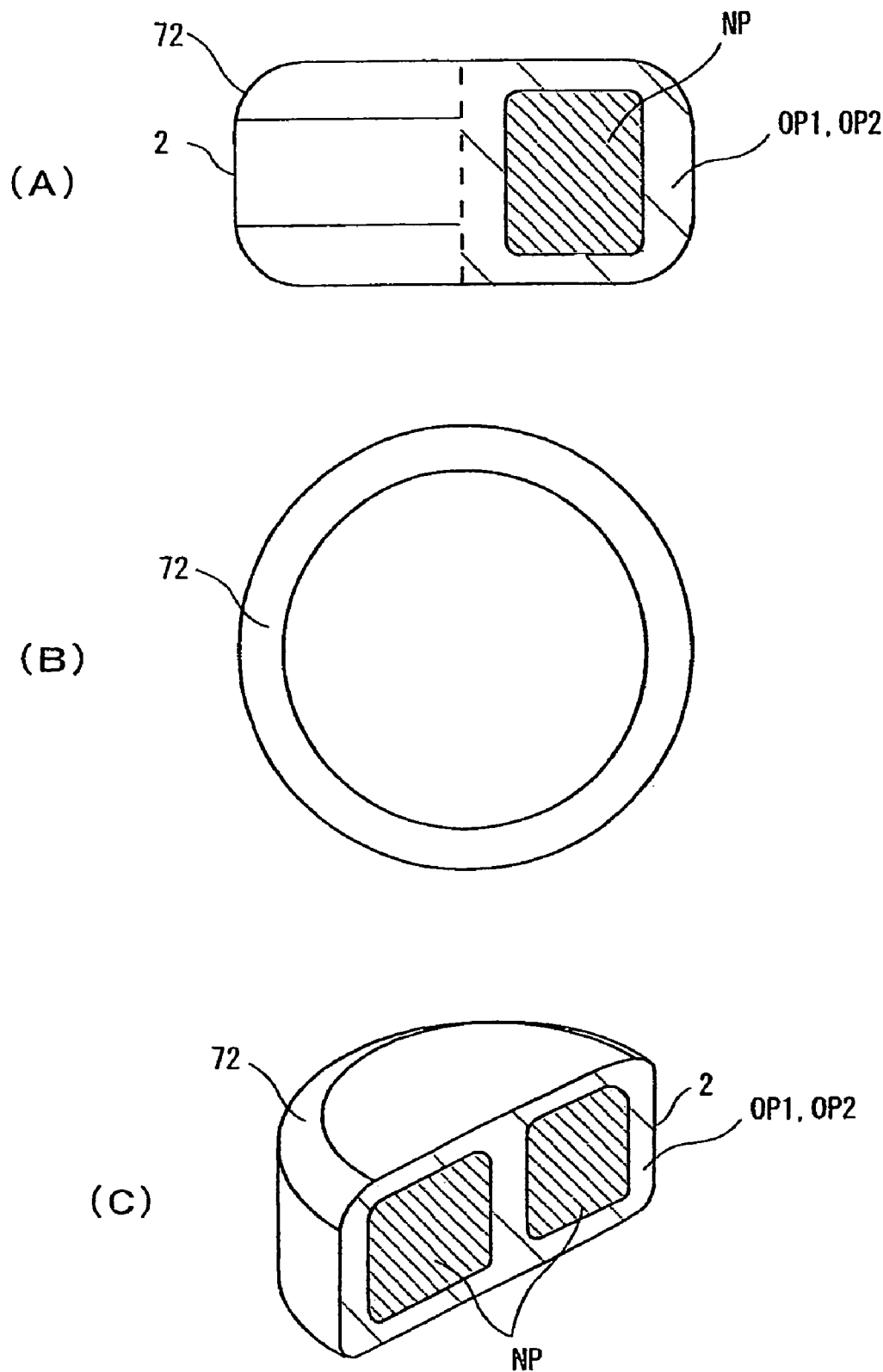
In FIG. 2 that illustrate an embodiment of a molded product manufactured by the manufacturing method and apparatus of a multi-core press-coated molded product of the present invention.

It should be noted that outer punch tip portions (6B, 7B) correspond to a circumferential edge 72 of a completed molded product shown in FIG. 2 and may be flat depending on the embodiment of the molded product. If they are not flat as shown in FIG. 1, it is preferred, to prevent contamination between the powder or granular particles for the outer layer and the cores, that steps (FIGS. 1D and 1H) of removing residual powder or granular particles 57 and 58 remaining on an upper surface 7B of the lower outer punch be further added during compression molding of the first outer layers OP1 (during temporary molding) or thereafter and during compression molding of the first outer layers OP1 and the cores NP (during temporary molding) or thereafter. The residual powder or granular particles can be removed using a compressed air injection and suction device, as shown, for example, in FIG. 8, a brush, a scraper, etc. or a combination thereof. These are referred to as residual powder or granular particles removal means.

Figure 9:
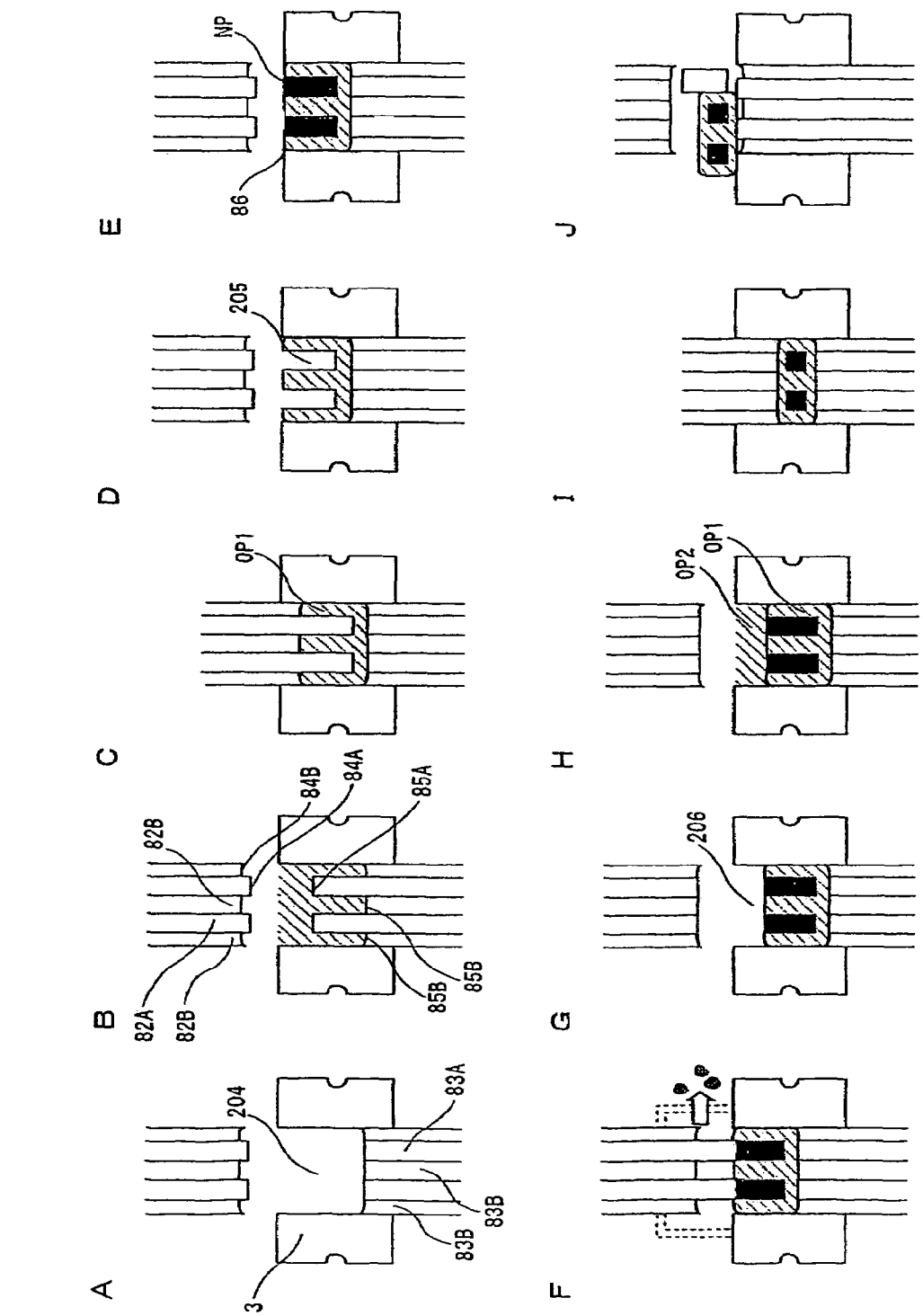
FIG. 9 illustrates explanatory views of punch tip operations showing a second example of the manufacturing method of a multi-core press-coated molded product of the present invention (shading as cross section omitted)

Next, a detailed description will be given below of a second example of the method of manufacturing the multi-core press-coated molded product of the present invention mainly with reference to FIG. 9. Here, temporary compression is also used as midway compression operation. It is to be understood that temporary compression operation of the powder or granular particles for the first outer layer OP1 cannot be omitted in the present method. Instead, it is possible to omit temporary compression operation of the powder or granular particles for the cores NP.

First, with the lower center punch (lower center and outer punches 83A and 83B) lowered (FIG. 9A), the powder or granular particles for the first outer layer OP1 is supplied into a first outer layer space 204 above the lower punch within the die. The lower center punch 83A or the lower center and outer punches 83A and 83B are raised to predetermined positions as necessary, thus removing the powder or granular particles for the first outer layer OP1 overflowing from the die 3. Here, it is preferred that the lower center punch be pushed out in advance to ensure that the portion corresponding to the recesses of the pot-shaped molded product of the outer layer is charged with a lesser quantity of powder or granular particles. Then, the upper punch (upper center and outer punches 82A and 82B), with the upper center punch 82A projecting toward the lower punch, and the lower punch (both the lower center and outer punches 83A and 83B) are moved to engage each other for temporary compression, thus temporarily molding the pot-shaped first outer layer OP1 (FIG. 9C).

Next, the powder or granular particles for the cores NP is supplied into core spaces 205 within the temporary molded product of the pot-shaped first outer layer OP1 (FIG. 9E), and the excess powder or granular particles for the cores NP is removed as necessary. Then, the upper center punch 82A is moved toward the lower punch for temporary compression of the powder or granular particles for the cores NP, thus temporarily molding the cores NP or the cores NP and the first outer layer OP1 (FIG. 9F). Here, the upper outer punch 82B may be concurrently moved toward the lower punch for concurrent temporary compression of the temporary molded product of the first outer layer OP1.

Further, with the temporary molded product of the fist outer layer OP1 and the cores NP held on the lower punch within the die, the powder or granular particles for the second outer layer OP2 is supplied into a second outer layer space 206 above the temporary molded product of the first outer layer OP1 and the cores NP within the die by lowering the lower punch as necessary (FIG. 9H). The lower punch is raised to a predetermined position as necessary, thus removing the excess powder or granular particles for the second outer layer OP2 out of the die 3. Then, the upper and lower punches are moved in mutually approaching directions for precompression (temporary compression) of the entire molded product consisting of the first outer layer, the cores and the second outer layer as necessary, eventually followed by main compression (FIG. 9I). The step shown in FIG. 9J is for ejecting the completed molded product.

In the present method, a normal punch with no double structure may be used for the lower punch. In this case, powder or granular particles charging is slightly problematic because the lower center punch cannot be pushed out in FIG. 9B. However, there are no problems when the cores are small in quantity.

In the second example of the method of manufacturing the multi-core press-coated molded product of the present invention, it is preferred, to prevent contamination between the powder or granular particles for the outer layer and the cores, that the step (FIG. 9F) of removing the residual powder or granular particles 86, that may adhere to the upper portion of the temporary molded product of the first outer layer OP1 during supply of the powder or granular particles for the cores NP, be further added after supply of the powder or granular particles for the cores NP or during compression molding (during temporary molding) of the cores NP (or the cores and the first outer layer) or thereafter. It should be noted that both temporary compression and residual powder or granular particles removal steps are concurrently performed in FIG. 9F. The present removal step conforms to the first example of the manufacturing method.

Figure 10:
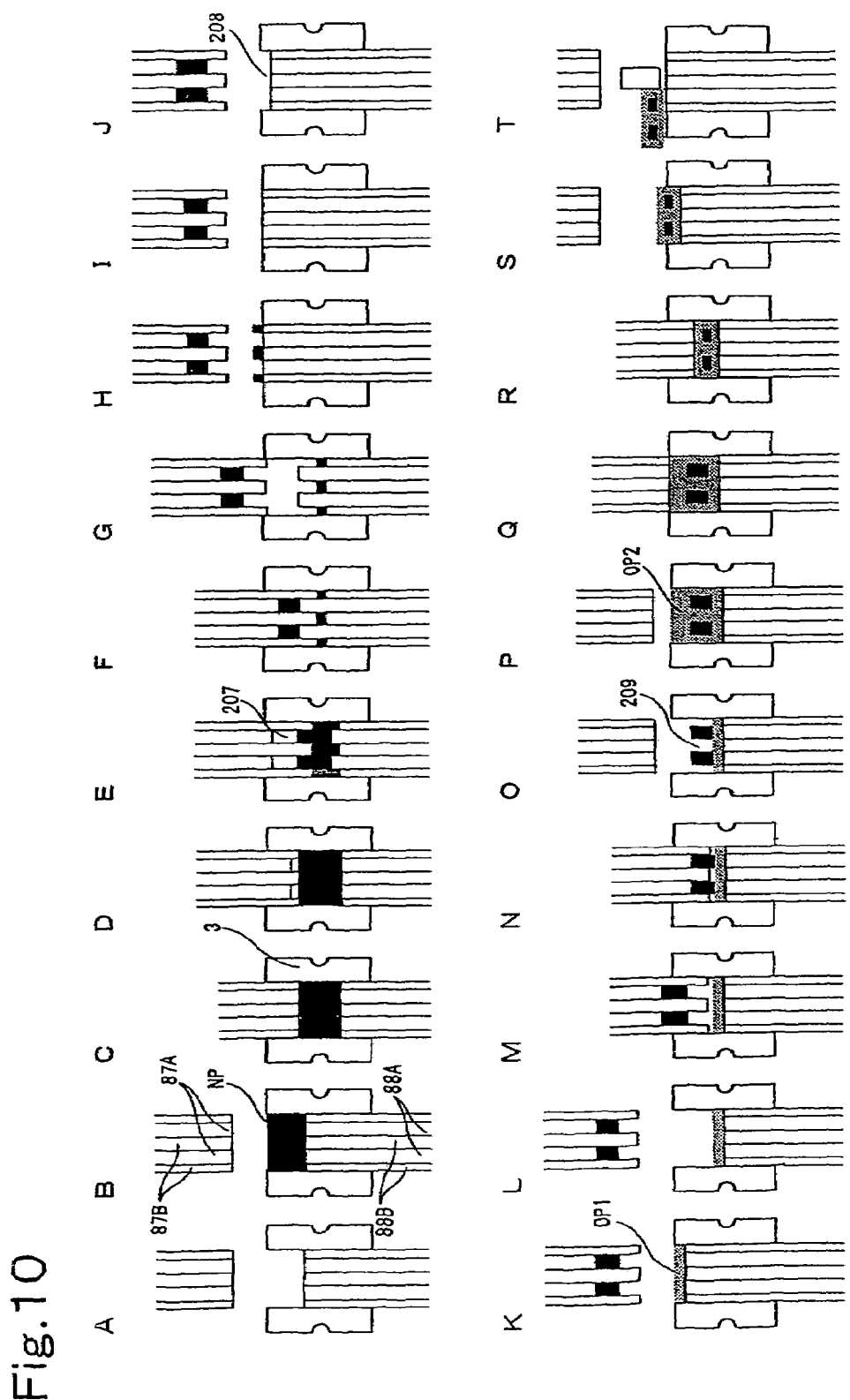
FIG. 10 illustrate explanatory views of punch tip operations showing a third example of the manufacturing method of the multi-core press-coated molded product of the present invention (shading as cross section omitted)

Next, a brief description will be given below of a third example of the method of manufacturing the multi-core press-coated molded product of the present invention mainly with reference to FIG. 10. Here, temporary compression is also used as midway compression operation. It should be understood that temporary compression operation of the powder or granular particles for the cores NP cannot be omitted in this embodiment method. Compression operation of a powder or granular particles for the first outer layer OP1 is arbitrary.

First, with a lower punch (lower center and outer punches 88A and 88B) lowered (FIG. 10A), the powder or granular particles for the cores NP is supplied into a space above the lower punch within the die, and the lower punch is raised to a predetermined position as necessary, thus removing the powder or granular particles for the cores NP overflowing from the die 3 (FIG. 10B) The upper punch (both the upper center and outer punches 87A and 87B) is lowered and inserted into the die, and with the powder or granular particles for the cores held in the space enclosed by the upper and lower punches as well as the die (FIG. 10C), the upper outer punch 87B is pushed out toward the lower outer punch 88B or the upper center punch 87A is pulled in or the upper outer punch 87B is pushed out while pulling in the upper center punch 87A, thus creating a core spaces 207 enclosed by the upper center and outer punches 87A and 87B (FIG. 10D). The lower center punch 88A is pushed out into the spaces, charging the powder or granular particles for the cores (FIG. 10E). Further, the lower center punch 88A is pushed out toward the upper center punch 87A and the upper and lower center punches 87A and 88A are moved to engage each other for temporary compression, thus molding the temporary molded products of the cores in the spaces enclosed by the upper outer punch 87B and below the upper center punch 87A (FIG. 10F). Then, with the temporary molded products of the cores held by the upper center and outer punches 87A and 87B, the upper punch is raised out of the die (FIG. 10G) while simultaneously raising the lower punch toward the upper punch, thus removing the excess powder or granular particles for the cores NP (FIGS. 10H and 10I).

Next, the powder or granular particles for the first outer layer OP1 is supplied (FIG. 10K) into a first outer layer space 208 above the lower punch within the die (FIG. 10J), and the excess powder or granular particles for the first outer layer OP1 is discharged as necessary. Then, the lower punch holding the powder or granular particles for the first outer layer OP1 is lowered (FIG. 10L) while simultaneously lowering the upper center and outer punches 87A and 87B holding the temporary molded products of the core, thus inserting the upper punch into the die (FIG. 10M). Here, the upper center punch 87A is pushed out downward, thus releasing the temporary molded products of the core onto the powder or granular particles for the first outer layer OP1 (FIGS. 10N and 10O). Next, the powder or granular particles for the second outer layer OP2 is supplied (FIG. 10P) into a second outer layer space 209 above and around the temporary molded products of the core within the die (FIG. 10O). The lower punch is moved to a predetermined position as necessary, thus removing the excess powder or granular particles for the second outer layer OP2 out of the die 3. Then, the upper and lower punches are moved to engage each other for precompression (temporary compression) of the entire molded product consisting of the cores and the first and second outer layers as necessary (FIG. 10Q), eventually followed by main compression (FIG. 10R). In the step shown in FIG. 10T the completed molded product is ejected from the punch.

Figure 11:
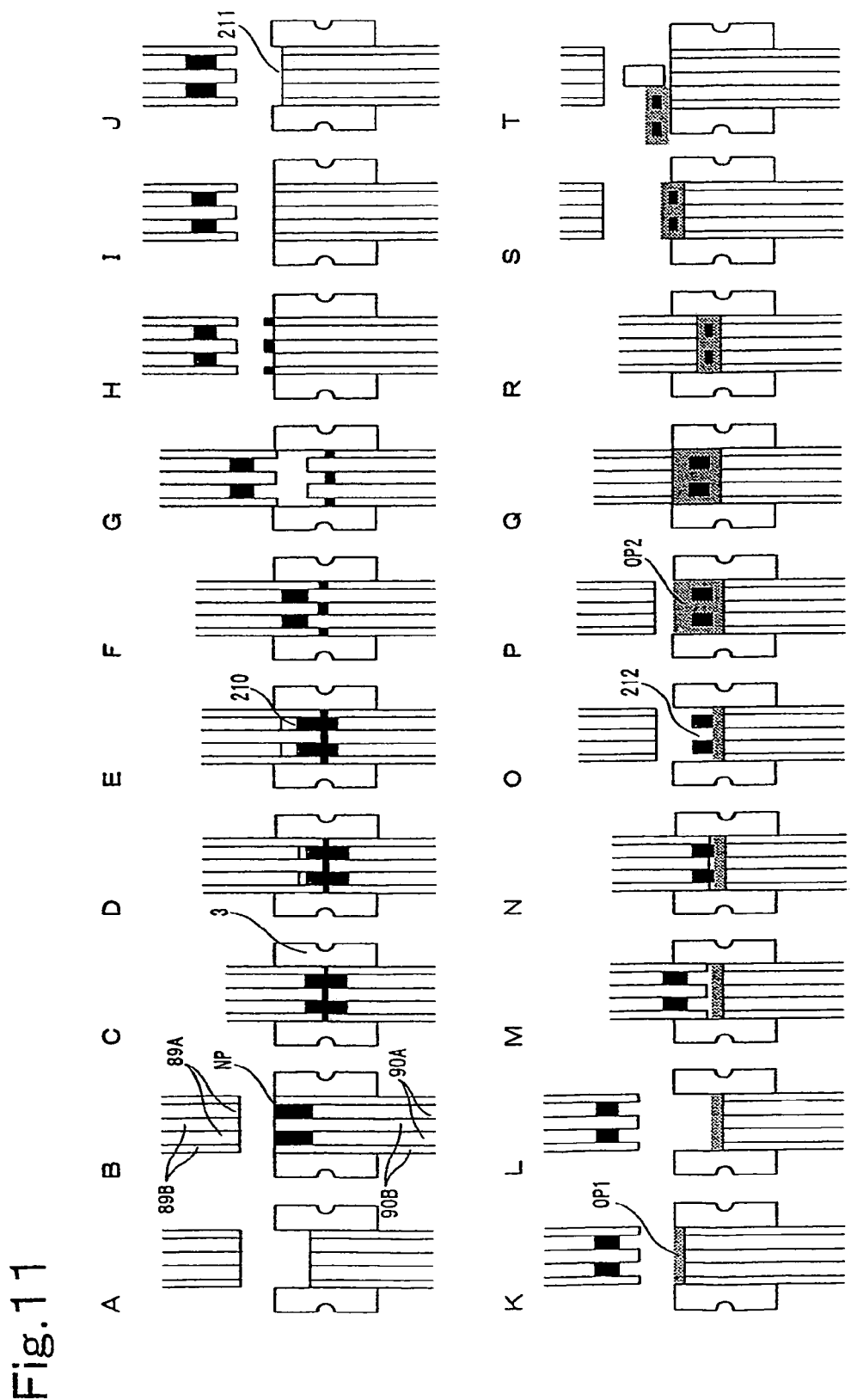
FIG. 11 illustrate explanatory views of punch tip operations showing a partial modification of the third example of the manufacturing method of the multi-core press-coated molded product of the present invention (shading as cross section omitted)

It should be noted that according to the third example of the method of manufacturing the multi-core press-coated molded product of the present invention, it is possible, as shown in FIG. 11, to charge the powder or granular particles for the cores NP into a space above a lower center punch 90A and enclosed by a lower outer punch 90B, and lower the upper punch (upper center and outer punches 89A and 89B), thus transferring the powder or granular particles for the cores NP from within the lower outer punch 90B into the upper outer punch 89B.

The method of manufacturing the multi-core press-coated molded product according to the present invention can be implemented by compression molding means characterized in having punches above and below a die, with at least the upper punch consisting of a center punch whose tip portion is split into two or more parts and an outer punch enclosing the outer perimeter of the center punch and whose tip portion fills the gap at the tip portion of the center punch and both the center and outer punches being slidable and manipulatable for compression operation. The manufacturing method according to the present invention can be readily performed by the punches and die and a hydraulic press although a rotary powder compression molding machine of the present invention described later is among such compression molding means. That is, the compression molding means can be readily implemented by performing, in accordance with the sequence of steps of the present invention, a series of steps—steps of manually and/or automatically moving the upper and lower punches or the center and outer punches to predetermined positions, charging with the intended powder or granular particles (powder or granular particles for the outer layers and the cores) and pressing the powder or granular particles so as to sandwich them from above and below.

A description will be given next of the punch used in the present invention.

The punch used in the present invention has a double structure consisting of a center punch whose tip portion is split into two or more parts and an outer punch enclosing the outer perimeter of the center punch and whose tip portion fills the gap at the tip portion of the center punch, with the outer shape of the tip portion of the center punch being approximately identical to the inner shape of the die and further the outer shape of the tip portion of the center punch being approximately identical to the outer shape of the cores and the inner shape of the tip portion of the outer punch. Further, both the center and outer punches are slidable and manipulatable for compression operation. Here, the center and outer punches are slidable independently of each other, except for those portions that slide by coordination of the two punches.

Figure 3:
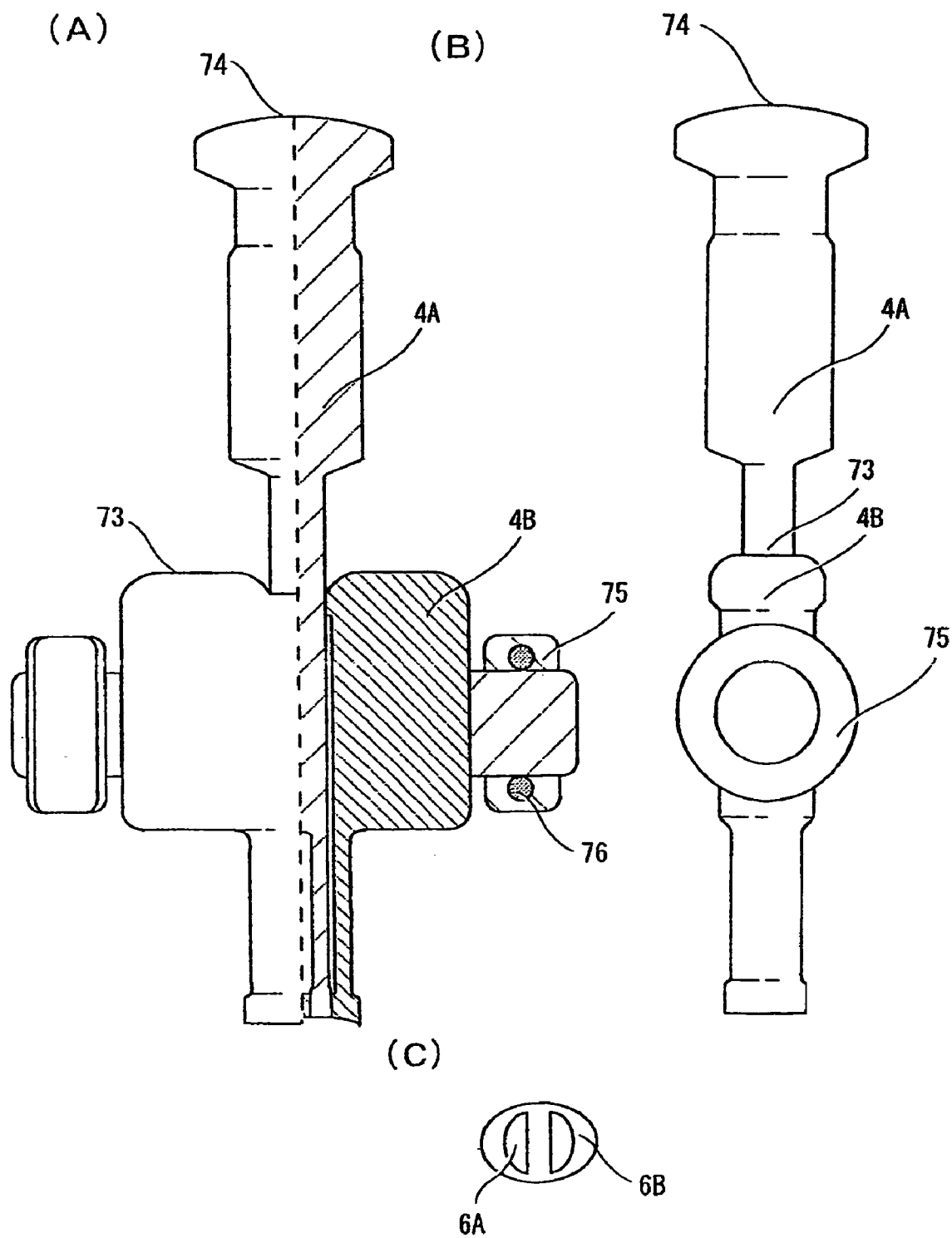
In FIG. 3 that that illustrates an example of a double-structured punch used in the present invention showing an upper punch.

For example, in a punch structured as shown in FIG. 3, the tip portion is split into two parts and is provided with a center and outer punches 4A and 4B, an outer punch compression head 73, a center punch compression head 74 and an outer punch vertical sliding motion adjustment roller 75. It should be noted that a single center punch is branched at the tip rather than having independent punches. Such a punch is preferred because it is possible to make the amount of pressure transferred and the pressure transfer speed the same in order to maintain the same moldability for a plurality of cores. Further, the punch is also advantageous in terms of punch manufacture and operation because it does not result in a complicated form due to its structure. It is also possible to use, for the punch, an integrally structured shell portion separate from the tip portions all of which can be integrated into one piece by fastening them. If individual adjustment of the amount of respective cores to be charged is necessary, a plurality of independent center punches are naturally needed instead of a single center punch branched at the tip.

Figure 7:
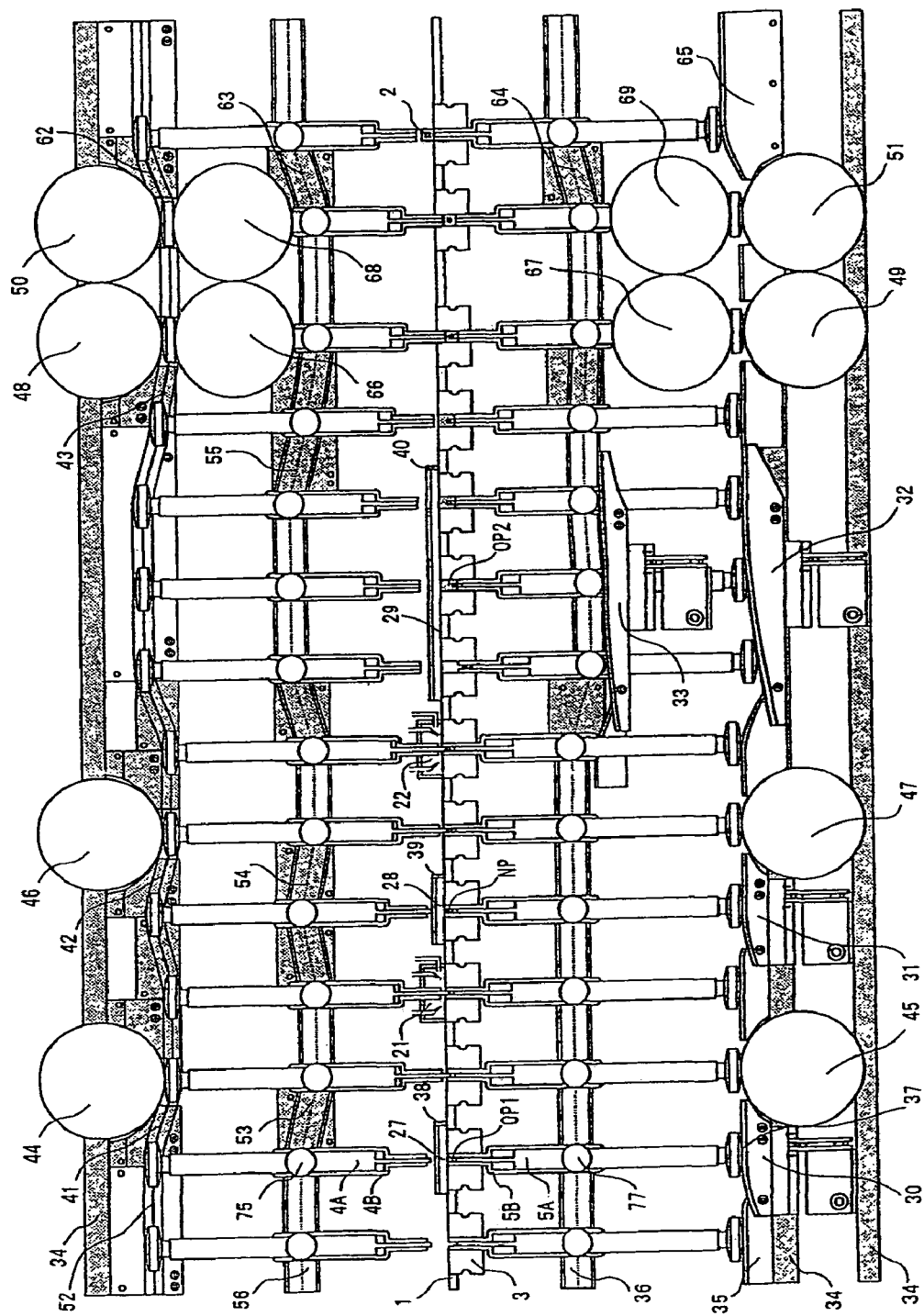
FIG. 7 illustrates a schematic view including a partial sectional view and showing the operational mechanism of upper and lower punches by developing the turntable in an embodiment of the rotary compression molding machine of the present invention.

For the punch of the present invention, compression of the portion corresponding to the cores with large compression area is carried out by pressing the center punch compression head 74 with compression rollers (44, 46, 48, 50 in FIG. 7), whereas compression of the outer perimeter portion of the molded product is performed by pressing the outer punch compression head 73 with compression rollers (66, 68 in FIG. 7). This allows for compression operation using the center and outer punches. It should be noted that if independent center punches with no branched tips are used, the number of center punch compression heads 74 correspond with the number of tip portions.

While the vertical sliding motion of the center punch is controlled by a normal method mainly using the center punch track and the punch bottom portion (same portion as the center punch compression head 74), the vertical sliding motion adjustment roller 75 that comes in direct contact with the outer punch track to allow vertical sliding motion of the outer punch is provided. Preferably, a plurality of bearings 76 are provided within the rollers to allow rotation of the rollers and smooth vertical sliding motion of the outer punch.

Here, the vertical sliding motion adjustment roller 75 is arranged outside the outer punch compression head 73, with the vertical sliding motion adjustment roller 75 separated from the outer punch compression head 73. This allows the compression roller to apply pressure only to the outer punch compression head 73 without applying direct pressure to the vertical sliding motion adjustment roller 75, thus preventing breakage of the bearings 76 within the vertical sliding motion adjustment roller 75. In compression operation, it is possible to apply pressure to the outer punch more from the side of the center punch, thus allowing efficient transfer of pressure from the compression roller to the powder or granular particles. Contact portions of the compression rollers of the center and outer punches (the outer punch compression head 73 and the center punch compression head 74) are vertically separated from each other, thus preventing interference between the compression rollers of the center and outer punches.

While FIG. 3 show the upper punch, the same holds true for the lower punch. The difference is a longer length of the tip portion of the lower punch is inserted into the die.

Figure 4:
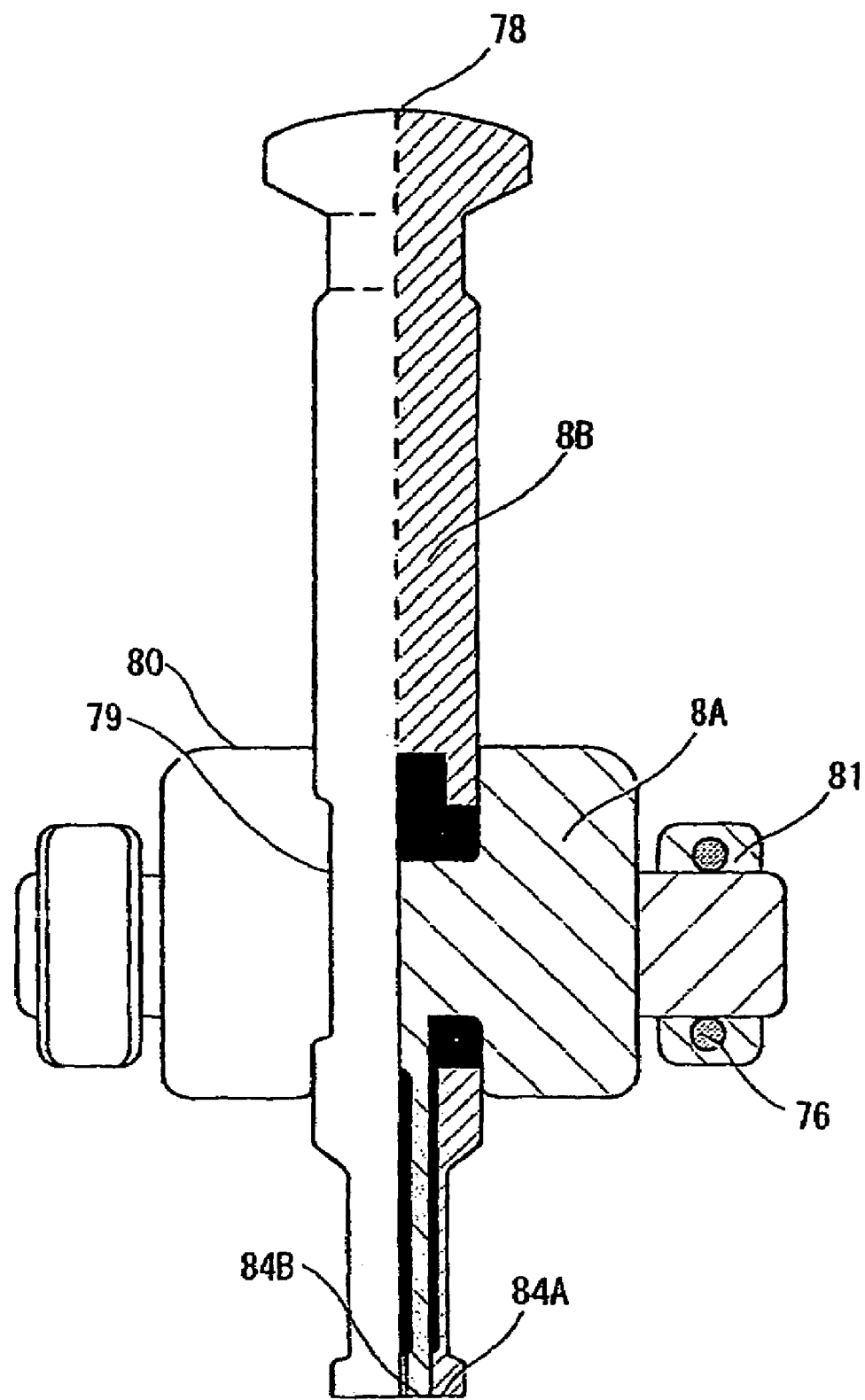
FIG. 4 illustrates an example of a double-structured punch used in the present invention showing an upper punch—a vertical sectional view (right half) and a schematic view (left half)—that controls its center and outer punches in reverse as compared with the punch shown in FIG. 3.

Alternatively, the double punch used in the present invention may be that corresponding to FIG. 4 in which the motions of the center and outer punches are respectively controlled in reverse that is, the punch controls the motion of the center punch with the vertical sliding motion adjustment roller and the track and the motion of the outer punch with the punch bottom portion (same portion as the outer punch compression head 78) and the track. The punch is, as shown in FIG. 4, characterized in that an opening portion (an outer punch opening portion 79) is provided on the main body of the outer punch and that a center punch compression head 80 integral with the center punch and a center punch vertical sliding motion adjustment roller 81 project from the opening portion. A description of the punch will be omitted since the same holds true for the punch as for the punch of FIG. 3, except that the motion of the center and outer punches are respectively controlled in reverse.

In addition to the type whose center punch has a tip portion split into two parts, the punch used in the present invention may have a center punch with a tip portion split into three, four or more parts.

Further, as for the score line to provide a dividable multi-core press-coated molded product, it suffices for the score line to conform to the conventional methods currently used In detail, in the case of a two-core equally dividable molded product, a convex shape (corresponding to the score line portion) is provided on the centerline along the shorter diameter of the surface of the lower outer punch 5B and/or the upper outer punch 4B. The convex shape forms a concave recess on the centerline along the shorter diameter, thus making it possible to form a score line on the molded product. It should be noted that if a convex shape is formed on the surface of the lower outer punch 5B or the upper outer punch 4B, the molded product will have a score line on one side, whereas if a convex shape is formed on the surfaces of both the lower and upper outer punches 5B and 4B, the molded product will have a score line on both sides. It is also possible to provide a score line on a portion of the molded product other than that described above and to provide a plurality of score lines.

To describe, in further detail, the apparatus for manufacturing the multi-core press-coated molded product of the present invention, descriptions will be given in succession beginning with a conventional rotary compression molding machine.

Figure 5:
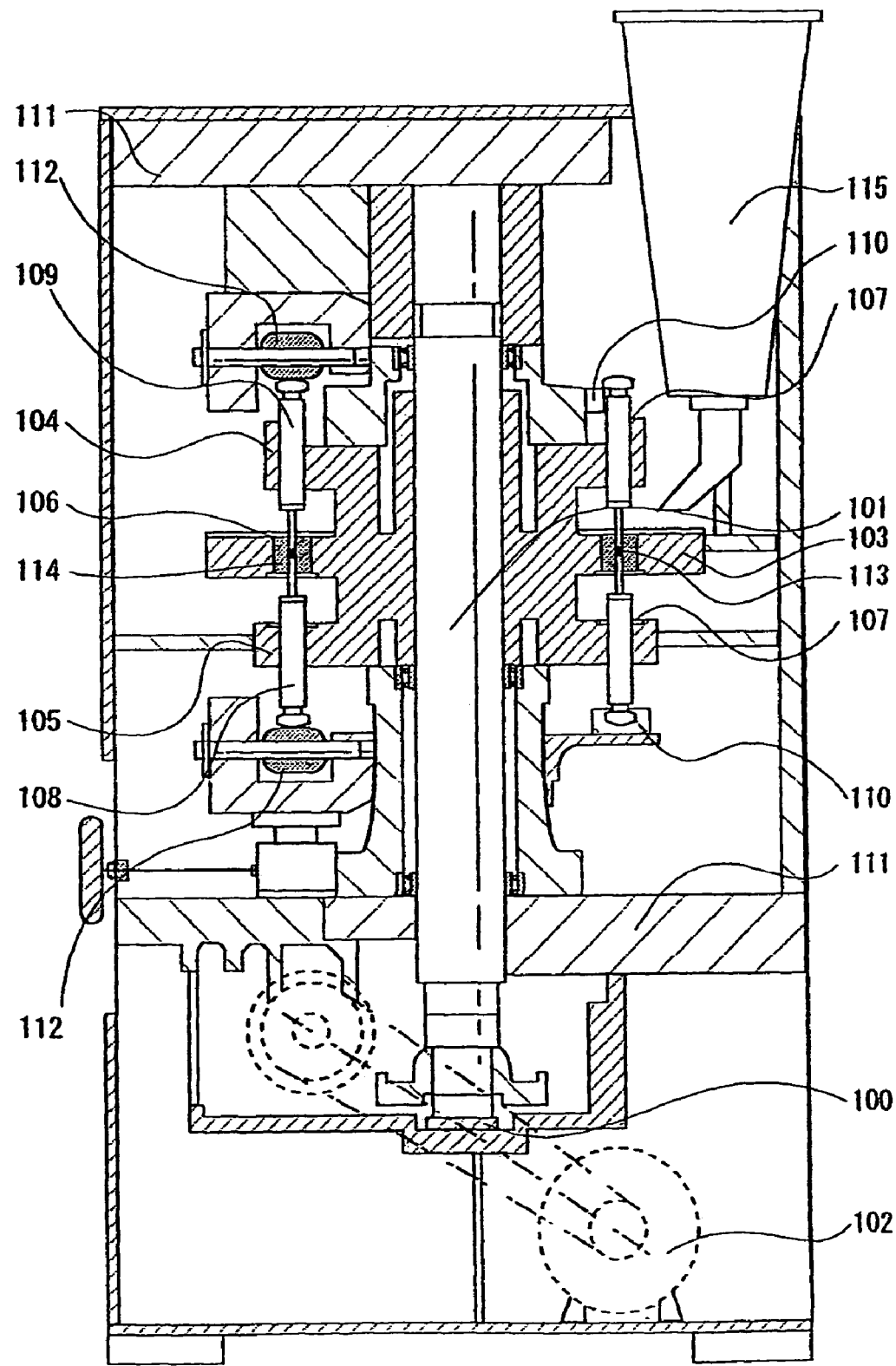
FIG. 5 illustrates an overall front sectional view of a common rotary compression molding machine, except that the sectional views of the punch, the vertical shaft, and the hopper are not shown.

For example, if a shaft-driven rotary compression molding machine has a vertical shaft 101, supported by a bearing 100, arranged at the center portion of the main body frame 111, with a motor 102 transmitting rotational drive force to the vertical shaft and a turntable 103—splittable into two functional parts—fixed near the vertical shaft, as shown in FIG. 5. Further, there are provided an upper punch holding portion 104, located on the upper portion of the turntable, for holding an upper punch so as to be vertically slidable and a lower punch holding portion 105, located on the lower portion of the turntable, for holding a lower punch so as to be vertically slidable such that the turntable 103 is sandwiched between the upper and lower punch holding portions 104 and 105. On the turntable 103, there is a die portion made up of a plurality of die mounting holes 106, for fitting the die 114 so as to be detachable/reattachable, that are provided along the same circumference. On each of the upper and lower punch holding portions 104 and 105, there is a plurality of punch holding holes 107 drilled for holding the upper and lower punches so as to be slidable. Each of the die mounting holes 107 and the punch holding holes 106 is drilled on the turntable such that the lower punch 108, the upper punch 109 and the die 114 are arranged vertically with their center lines aligned. Tracks 110 are provided correspondingly for track contact portions of the upper and lower punches 109 and 108, and the punches move vertically on the tracks as they engage with and are guided by respective cams which will be discussed later. The die 114 has a die hole 113 provided vertically through the die into which the tips of the upper and lower punches 109 and 108 are inserted. It should be noted that 112 represents a compression roller while 115 a hopper in FIG. 5.

In addition to shaft-driven rotary compression molding machines, there are other types thereof such as external gear-driven (external gear type) and internal gear-driven (internal gear type) rotary compression molding machines in which the rotational drive force is transmitted by equipping the turntable with a gear.

Next, a detailed description will be given of an embodiment of the apparatus corresponding to the first embodiment of the manufacturing method of the present invention (FIG. 1) together with operations of the portions thereof mainly with reference to FIGS. 6 and 7 and, as necessary, FIG. 1 as the apparatus for manufacturing the multi-core press-coated molded product of the present invention that is the rotary compression molding machine.

Figure 6:
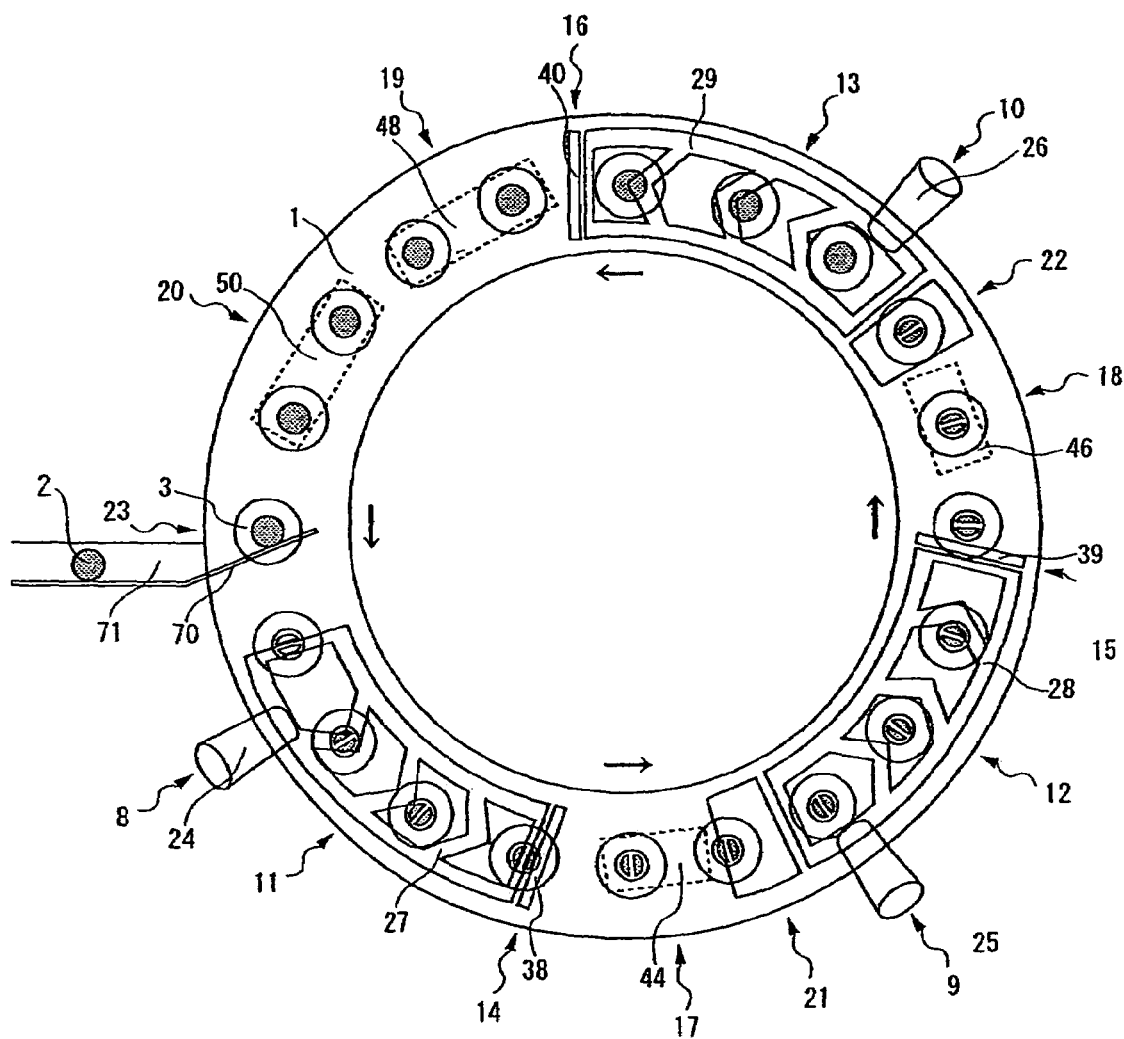
FIG. 6 illustrates a schematic plan view showing the top side of a turntable in an embodiment of the rotary compression molding machine of the present invention.

When viewed from above the turntable, powder or granular particles supply portions 8, 9 and 10, powder or granular particles charging portions 11, 12 and 13, powder or granular particles rubbing-cutting portions 14, 15 and 16, compression molding portions 17, 18, 19 and 20, residual powder or granular particles removal portions 21 and 22 and a product ejecting portion 23 are provided along the direction of rotation of a turntable 1 as shown in FIG. 6.

Description will be made on a mechanism-by-mechanism basis. The powder or granular particles supply portions (8, 9, 10 in FIG. 6) can be separated, according to the sequence of supply of powder or granular particles, into the portion 8 for supplying the powder or granular particles for the first outer layer OP1, the portion 9 for supplying the powder or granular particles for the cores NP, and the portion 10 for supplying the powder or granular particles for the second outer layer OP2, with the powder or granular particles supplied by natural fall or by a metered supply machine (not shown) from hoppers 24, 25 and 26 filled with the respective powder or granular particles.

The respective powder or granular particles supplied by the powder or granular particles supply portions are sent next to the powder or granular particles charging portions (11, 12, 13 in FIG. 6). The powder or granular particles charging portions are designed to charge each of the powder or granular particles for the first outer layer OP1, the cores NP and the second outer layer OP2, respectively into the first outer layer space 201, the core space 202 or the second outer layer space 203 (refer to FIG. 1). These portions are intended to hold fixed amounts of the respective powder or granular particles supplied from the powder or granular particles supply portions using open feed shoes 27, 28 and 29, provided on the turntable 1 and capable of both storing and supplying the powder or granular particles, and introduce each of the powder or granular particles held by the feed shoes 27, 28 and 29 into the first outer layer spaces 201, the core spaces 202 or the second outer layer space 203 (refer to FIG. 1) by lowering the lower center punch 5A using lowerers 30, 31 and 32 provided on a frame 34, and in certain circumstances, by lowering the lower outer punch 5B using a lowerer 33 provided on a lower outer punch track 36.

In detail, the powder or granular particles for the first outer layer OP1 is charged by lowering the lower center punch 5A within the first open feed shoe 27 on the turntable 1 (FIGS. 1A and 1B). Here, the lower outer punch 5B is maintained at a constant height with respect to the turntable by being moved on the lower outer punch track 36, installed so as to bring the extreme tip portion of the lower outer punch 5B to the same height as the surface of the turntable 1, using the vertical sliding motion adjustment roller 77 of the lower outer punch. On the other hand, the lower center punch 5A is moved on a lower center punch track 35 provided on the frame 34 using the lower center punch bottom portion 37 (substantially the same portion as the center punch compression head 74 as shown in FIG. 3) and further adjusted to a predetermined position using the first center punch lowerer 30 provided on the lower center punch track 35. The powder or granular particles for the first outer layer OP1 is thus introduced into the first outer layer spaces 201 enclosed by the lower outer punch 5B and above the lower center punch 5A.

Next, the powder or granular particles for the cores NP is charged by lowering only the lower center punch 5A within the second open feed shoe 28 on the turntable 1 as with the first outer layers OP1 (FIGS. 1E and 1F). Here, the lower outer punch 5B is maintained at a constant height with respect to the turntable by being moved on the lower outer punch track 36 installed so as to bring the extreme tip portion of the lower outer punch 5B to the same height as the surface of the turntable 1 using the vertical sliding motion adjustment roller 77 of the lower outer punch. On the other hand, the lower center punch 5A holding the temporary molded products of the first outer layer on a lower center punch upper end surface 7A is moved using the lower center punch bottom portion 37 that moves on the lower center punch track 35 provided on the frame 34 and further lowered using the second center punch lowerer 31 provided on the lower center punch track 35. The powder or granular particles for the cores NP is thus introduced into the core spaces 202 enclosed by the lower outer punch 5B and above the temporary molded products of the first outer layer.

Further, the powder or granular particles for the second outer layer OP2 is charged by lowering both the lower center punch 5A holding the temporarily molded first outer layers OP1 and cores NP and the lower outer punch 5B or the lower outer punch 5B within the third open feed shoe 29 on the turntable 1 (FIGS. 1I and 1J). Here, the lower outer punch 5B is lowered using the lower outer punch lowerer 33 provided on the lower outer punch track 36. On the other hand, the lower center punch 5A is moved using the lower center punch bottom portion 37 that moves on the lower center punch track 35 provided on the frame 34 and lowered using the third center punch lowerer 32 provided on the lower center punch track 35. The powder or granular particles for the second outer layer OP2 is thus introduced into the second outer layer space 203 created above and around the temporary molded products of the first outer layer OP1 and the cores NP within the die 3 by lowering both the lower center and outer punches 5A and 5B or only the lower outer punch 5B.

Although the third open feed shoe 29 as shown in FIG. 7 appears larger than the other open feed shoes in FIG. 7, this is intended only to more clearly show the details described hereafter. It should be noted that, in place of the open feed shoes, agitation feed shoes may be employed to forcefully charge the powder or granular particles into the die using agitation vanes (installed at the same positions as the open feed shoes; not shown).

The die and punches charged with the powder or granular particles by the powder or granular particles charging portions next enter the powder or granular particles rubbing-cutting portions (14, 15, 16 in FIG. 6). The powder or granular particles rubbing-cutting portions adjust the amount of powder or granular particles to be supplied and changed for the first outer layer OP1, the cores NP and the second outer layer OP2, as described above, to a fixed predetermined amount. That is, the respective excess powder or granular particles overflowing from the given spaces are rubbed and cut for removal by the rubbing-cutting plates 38, 39 and 40 as the lower center punch 5A or both the lower center and outer punches 5A and 5B are raised to predetermined positions by the lower outer and center punch tracks 36 and 35.

In detail, the powder or granular particles for the first outer layer OP1 is rubbed and cut by the rubbing-cutting plate 38 attached to the first open feed shoe 27 on the turntable 1. Here, with the extreme tip portion of the lower outer punch 5B level with the surface of the turntable 1, the lower center punch 5A is raised to a predetermined position, thus causing the excess amount of the powder or granular particles for the first outer layer OP1 charged into the first outer layer space 201 to overflow from the space. Further, the overflowing powder or granular particles for the first outer layer OP1 is rubbed and cut by the rubbing-cutting plate 38 attached to the open feed shoe 27, thus leaving behind a fixed amount of the charged powder or granular particles for the first outer layer OP1 (prior to and following FIG. 1B).

Next, the powder or granular particles for the cores NP is rubbed and cut by the rubbing-cutting plate 39 attached to the second open feed shoe 28 on the turntable 1 as with the powder or granular particles for the first outer layer. Here, with the extreme tip portion of the lower outer punch 5B level with the surface of the turntable 1, the lower center punch 5A is raised to a predetermined position. This causes the excess amount of the powder or granular particles for the cores NP charged into the core spaces 202 to overflow from the space. Further, the overflowing powder or granular particles for the cores NP is rubbed and cut by the rubbing-cutting plate 39 attached to the second open feed shoe 28, thus leaving behind a fixed amount of the charged powder or granular particles for the cores NP (prior to and following FIG. 1F).

The powder or granular particles for the second outer layer OP2 is also rubbed and cut by the rubbing-cutting plate 40 attached to the third open feed shoe 29 on the turntable 1 as with the powder or granular particles for the first outer layer and the cores. Here, the temporary molded products of the first outer layer and the cores held by the lower center and outer punches 5A and 5B are pushed up into the powder or granular particles for the second outer layer OP2 supplied into the die 3 as the lower center punch 5A or both the lower center and outer punches 5A and 5B are raised to predetermined positions. This causes the excess amount of the powder or granular particles for the second outer layer OP2 to overflow. Further, the overflowing powder or granular particles for the second outer layer OP2 is rubbed and cut by the rubbing-cutting plate 40 attached to the third open feed shoe 29, thus leaving behind a fixed amount of the charged powder or granular particles for the second outer layer OP2 (following FIG. 1K).

The die and punches charged with predetermined amounts of the powder or granular particles next enter the compression molding portions (17, 18, 19, 20 in FIG. 6). The compression molding portions are intended to perform pre-compression or main compression on one of the powder or granular particles for the first outer layer OP1, the cores NP, the second outer layer OP2 or a combination of two or more thereof (including temporary molded products) using compression rollers (44 to 51, 66 to 69) held by the frame 34.

In detail, precompression of the powder or granular particles for the first outer layer OP1 or the temporary molded products of the first outer layer OP1 and the powder or granular particles for the cores NP is carried out by pressing using the upper and lower center punches 4A and 5A. Here, the upper center punch 4A is lowered by upper center punch lowering cams 41 and 42 furnished on an upper center punch track 52, and preferably the upper outer punch 4B is also concurrently lowered to a predetermined position by upper outer punch lowering cams 53 and 54 furnished on an upper outer punch track 56, thus inserting the tip of the upper center punch 4A into the space above the lower center punch 5A and enclosed by the lower outer punch 5B within the die 3. The powder or granular particles for the first outer layer OP1 charged into the given space or the temporary molded products of the first outer layer OP1 and the powder or granular particles for the cores NP are thus confined from above and below and pressed so as to be sandwiched between the upper temporary compression rollers 44 and 46 and the lower temporary compression rollers 45 and 47, thus molding a temporary molded product (FIGS. 1C and 1G). It should be noted that although not preferred, the compression molding portion of the powder or granular particles for the first outer layer OP1 may be omitted.

Precompression (temporary compression) of the temporary molded products of the first outer layer OP1 and the cores NP and the powder or granular particles for the second outer layer OP2 is carried out by pressing using the upper center and outer punches 4A and 4B (upper punch) and the lower center and outer punches 5A and 5B (lower punch). To insert the upper center and outer punches 4A and 4B into the die 3, the upper center and outer punches 4A and 4B are lowered to predetermined positions using an upper center punch lowering cam 43 furnished on an upper center punch track 52 and an upper outer punch lowering cam 55 furnished on the upper outer punch track 56, and inserting the tips thereof into the die 3. The temporary molded products of the first outer layer OP1 and the cores NP and the powder or granular particles for the second outer layer OP2 are confined so as to be sandwiched from above and below and press-molded in a preliminary fashion by the precompression roller 48 for the upper center punch, the preliminary compression roller 66 for the upper outer punch, a preliminary compression roller 49 for the lower center punch, and the precompression roller 67 for the lower outer punch.

In main compression following precompression (temporary compression), the molded product press-molded in a preliminary fashion is press-molded as is in a full scale manner by the main compression roller 50 for the upper center punch, the main compression roller 68 for the upper outer punch, the main compression roller 51 for the lower center punch and the main compression roller 69 for the lower outer punch (FIG. 1M). It should be noted that although not preferred, it is possible to use only the present main compression portion by omitting the preliminary compression portion of the molded products of the first outer layer OP1 and the cores NP and the powder or granular particles for the second outer layer OP2.

Next, the residual powder or granular particles removal portions (21, 22 in FIG. 6) are provided at the temporary compression portion of the powder or granular particles for the first outer layer OP1 or the cores NP or a portion immediately thereafter. As shown in FIG. 1, during the temporary compression step or immediately thereafter, the lower outer punch 5B is held such that the extreme tip portion thereof is maintained at the same height as the surface of the turntable 1, and with the upper center punch 4A inserted into the space within the lower outer punch 5B or with the upper center punch 4A raised and pulled out of the space within the lower outer punch 5B, the powder or granular particles 57 for the first outer layer OP1 or the powder or granular particles 58 for the cores, remaining on the upper end surface 7B of the lower outer punch and/or the temporary molded product, is removed by compressed air injection and suction, etc. It should be noted that the present residual powder or granular particles removal portions maybe omitted under certain circumstances. In particular, when a flat-surfaced molded product is made, the outer punch surface is also flat, thus requiring no residual powder or granular particles removal portions.

Figure 8:
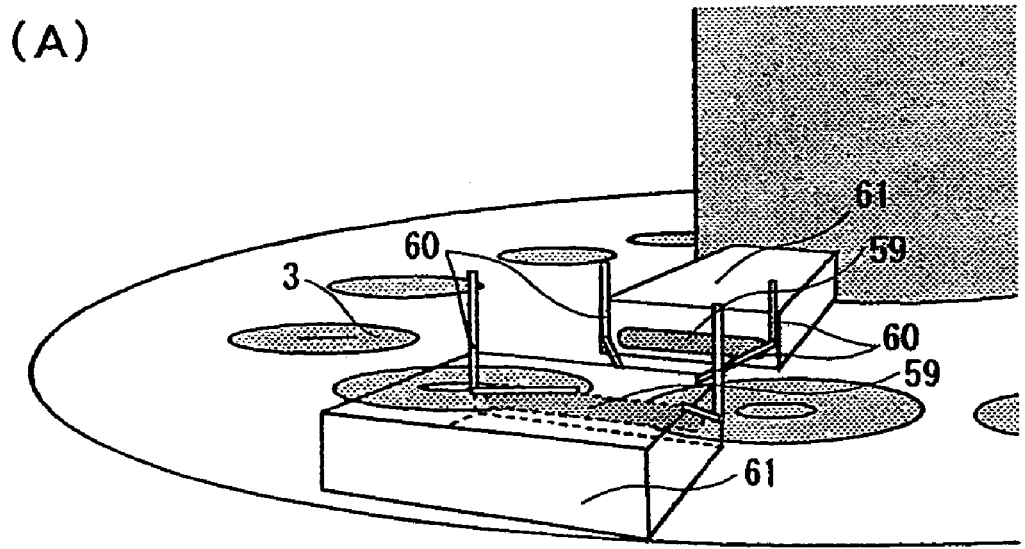
In FIG. 8 that illustrate a residual powder or granular particles removal device of the present invention.
Figure 8:
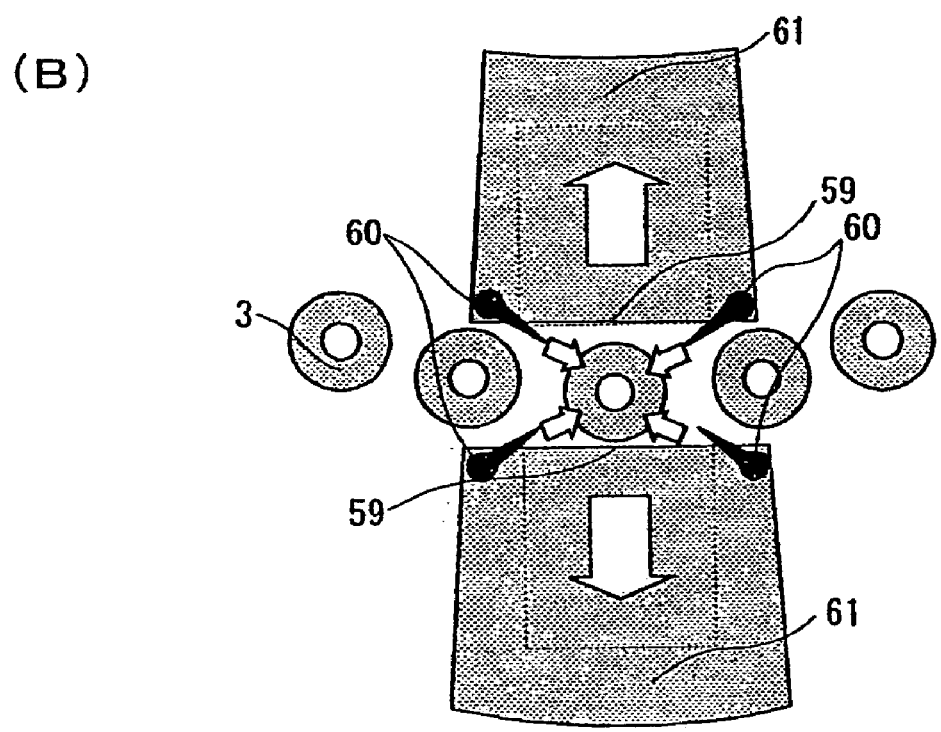

In detail, the upper end surface 7B of the lower outer punch 5B shown in FIG. 1 corresponds to the circumferential edge 72 of the finished product shown in FIG. 2, and the residual powder or granular particles 57 and 58 remain at the portion. The residual powder or granular particles 57 and 58 are impossible to remove by rubbing and cutting using the rubbing-cutting plates 38 and 39 of the open feed shoes or agitation feed shoes provided on the turntable 1 and, if left unremoved, cause a concern over contamination between the powder or granular particles for the first outer layer OP1 and the cores NP and that between the powder or granular particles for the cores NP and the second outer layer OP2. For the reason, in the present embodiment, the residual powder or granular particles 57 and 58 are removed by the first and second residual powder or granular particles removal portions 21 and 22 furnished on the turntable 1 following the temporary compression step (FIGS. 1D and 1H). A residual powder or granular particles removal device constituting the residual powder or granular particles removal portion comprises, for example as shown in FIG. 8, compressed air injection nozzles 60 for injecting compressed air onto the die surface from all directions and suction boxes 61 provided with suction holes 59 for aspirating the residual powder or granular particles, with the compressed air injection nozzles 60 and the suction boxes 61 arranged on and parallel with the surface of the turntable 1 so as to sandwich the die and the punches. The compressed air injection nozzles 60 inject compressed air onto the punches and the die from all directions and further the suction holes 59 near the die surface suck the residual powder or granular particles 57 and 58, keeping the residual powder or granular particles from flying outside for reliable removal thereof.

Alternative method of removing the residual powder or granular particles is by raising the upper center punch 4A with the temporary molded product held in the space inside the lower outer punch 5B and sucking the entire die from the upper end surface of the die (from the direction perpendicular to the turntable), thus removing the powder or granular particles 57 for the first outer layer OP1 or the powder or granular particles 58 for the cores NP remaining on the upper end surface 7B of the lower outer punch and/or the temporary molded products. It is necessary in the method that the temporary molded product not be sucked by suction, and temporary compression operation cannot be omitted from the outer layer molding step and the outer layer/core molding step. These residual powder or granular particles removal devices described above are the residual powder or granular particles removal devices of the present invention.

The final molded product is sent to the product ejecting portion (23 in FIG. 6) for ejection outside the molding apparatus. The product ejecting portion is designed to unload the product using a scraper 70 that guides to a chute 71 by pushing up the product as the lower center and outer punches 5A and 5B rise.

In detail, the upper center and outer punches 4A and 4B are raised along the rising sloped surface by upper center and outer punch raising cams 62 and 63, thus pulling the punch tips out of the die 3. Further, using lower center and outer punch push-up rails 65 and 64, the lower center and outer punches 5A and 5B are pushed up, thus completely pushing a molded product 2 out of the die 3. Here, it is preferred for easy ejection of the molded product that the tip surface of the lower outer punch 5B be maintained at the same level as the surface of the turntable and that the lower center punch 5A be pushed upward slightly more than the tip surface of the lower outer punch 5B (FIG. 1N). The molded product 2 that has been pushed out is scraped using the scraper 70 for ejecting outside the turntable 1 and then guided into the chute 71 for ejection of the product.

In the apparatus of the present invention shown in FIG. 7, the means for moving the center and outer punches refer to the tracks (the lower outer punch track 36, the lower center punch track 35, the upper outer punch track 56, the upper center punch track 52), the lowerers (the first center punch lowerer 30, the second center punch lowerer 31, the third center punch lowerer 32, the lower outer punch lowerer 33), the raising cams (the upper center and outer punch raising cams 62 and 63), the lowering cams (the upper center punch lowering cams 41, 42 and 43, the upper outer punch lowering cams 53, 54 and 55), the push-up rails (the lower center and outer punch push-up rails 65 and 64), the vertical sliding motion adjustment rollers (the vertical sliding motion adjustment rollers 77 and 75 of the lower and upper outer punches), the center punch bottom portion 37 and the bearings 76. On the other hand, means for allowing manipulation of the center and outer punches for compression operation refer to the compression rollers (the upper temporary compression rollers 44 and 46, the lower temporary compression rollers 45 and 47, the precompression roller 48 for the upper center punch, the precompression roller 66 for the upper outer punch, the precompression roller 49 for the lower center punch, the precompression roller 67 for the lower outer punch, the main compression roller 50 for the upper center punch, the main compression roller 68 for the upper outer punch, the main compression roller 51 for the lower center punch, the main compression roller 69 for the lower outer punch), and the outer punch compression head 73 and the center punch compression head 74 in FIG. 3. It should be noted that these include not only elements of the apparatus main body but also those of the punches.

As already described in relation to the punches, means for moving the center and outer punches or means for allowing manipulation of the center and outer punches for compression operation include not only the method as shown in FIG. 7 of controlling the motions of the outer punches by the vertical sliding motion adjustment rollers and tracks thereof and the motions of the center punches by the center punch bottom portions and tracks thereof (corresponding to the punches in FIG. 3) but also an alternative method that is a reverse thereof in which the motions of the center punches are controlled by the vertical sliding motion adjustment rollers and tracks and the motions of the outer punches by the punch bottom portions and tracks.

The apparatuses used in the second example (FIG. 9), the third example (FIG. 10) and the partial modification of the third example (FIG. 11) of the method of manufacturing the multi-core press-coated molded product of the present invention are basically the same as that described earlier used in the first example. Among the differences between the apparatuses are that, correspondingly with the difference in punch motions and compression operation, the layouts of means for moving the punches, compression means and such are naturally different, and the numbers of residual powder or granular particles removal portions are different.

So far, the method of manufacturing the multi-core press-coated molded product of the present invention and the apparatus therefore have been described. The multi-core press-coated molded product of the present invention will now be described with reference to embodiments. It should be noted that the molded product in the manufacturing example given below is an oblong tablet-type molded product assuming application to pharmaceuticals and dividable into two parts with a score line at the center portion.

MANUFACTURING EXAMPLE

Double-structured upper and lower punches were used, each having a score line and flat edge angle and consisting of a football-shaped outer punch whose tip was 16.0 mm in longer diameter and 8.0 m in shorter diameter and a center punch on the inside thereof with two circular tips of 6.0 mm in inner diameter that are branched at a 2 mm spacing, with the center and outer punches being arranged such that the minimum distance between the outer circumferences of the center and outer punches is 1.0 mm or more. Each punch surface was coated with a small amount of magnesium stearate (TAIHEI CHEMICAL INDUSTRIAL). A die and these punches were combined, and first with the lower center punch lowered, 30 mg of a mixture of hydroxypropyl methylcellulose (HPMC 60SH-4000: Shinetsu Chemical) and polyethylene glycol 6000 (PEG6000: NOF CORPORATION) mixed in a 9:1 ratio for the outer layer was respectively supplied into spaces enclosed by the lower outer punch and above the lower center punch. By moving the upper and lower center punches in mutually approaching directions, temporary compression was manually conducted to such an extent that the surface became flat. Next, 50 mg of thoeophyline (SHIZUOKA COFFEIN) was supplied respectively into two spaces above the temporary molded products of the mixture for the outer layer and enclosed by the lower outer punch, and temporary compression was manually conducted by moving the upper and lower center punches to engage each other to such an extent that the molded product could be maintained. Further, the remaining 140 mg of the mixture for the outer layer (same as above) was supplied into the space above and around the molded products made up of the mixture for the outer layer and thoeophyline such that the temporary molded products of thoeophyline was completely covered by the mixture for the outer layer. Then, by moving the upper and lower punches to engage each other, tabletting was conducted at a compression pressure of about 700 kg—this time using a hydraulic manual press (HP-3P: Iuchi Seieido), as a result of which, a molded product (undivided molded product) was obtained. The present molded product was readily divided into equal halves simply by holding both ends of the molded product with fingers with the division line at the center and pressing and bending the molded product toward the center. No core exposure was observed in the dividable molded product.

RELEASE PROPERTY EVALUATION

Three types of molded products produced according to the manufacturing example—a single undivided molded product, a single divided molded product divided at the score line and two divided molded products divided at the division line—were evaluated in conformance with the Dissolution Test of the General Tests, Processes and Apparatus of the Japanese Pharmacopoeia, Thirteenth Edition in order to assess the effect of division on the release property. It should be noted that purified water was used as the solvent and that, to prevent the tablets from adhering to the test vessel, the molded products were placed in a sinker conforming to the Japanese Pharmacopoeia for dissolution test. The amount of thoeophyline released was calculated by measuring, with a flow cell UV system (Shimadzu: UV-1600), the absorbance of given amounts of the liquids under test sampled using a dissolution tester (TOYAMA CHEMICAL: NTR-6100A).

Figure 12:
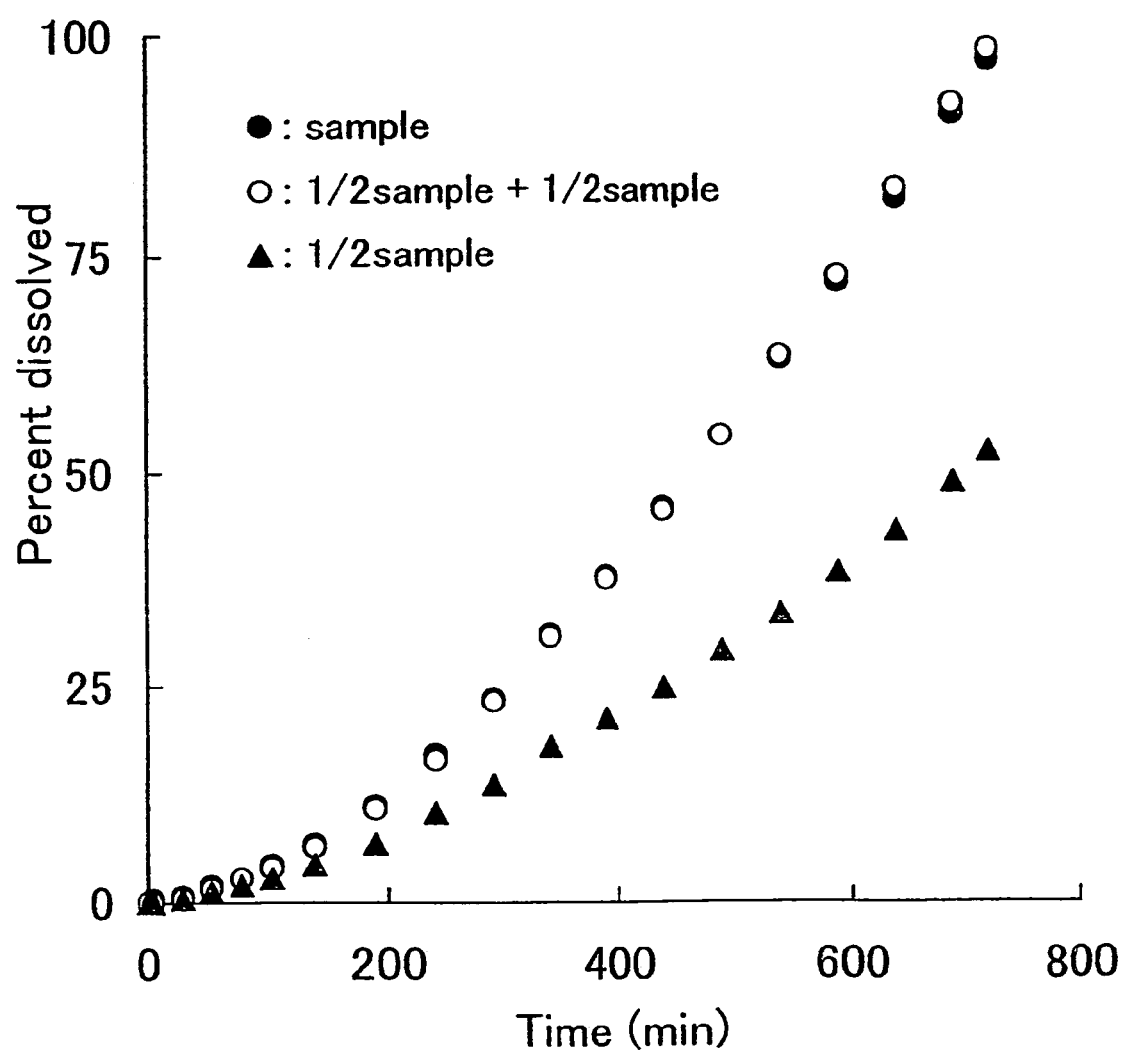
FIG. 12 illustrates a graph showing dissolution test results of a dividable multi-core press-coated molded product according to the present invention for comparing of when the molded product is divided and not divided.

The results are shown in FIG. 12. It should be noted that "●", "○" and "◆" respectively indicate the release curves of the undivided molded product, the two divided molded products and the single divided molded product.

It was discovered from FIG. 12 that, in the case of the undivided molded product, thoeophyline was gradually released over approximately 12 hours and that the release curve for the two divided molded products was also controlled by the coating. Further, it was also found from a close match of the thoeophyline release curves for the two divided molded products and the undivided molded product that the thoeophyline releasing rate was controlled by the coating in both of the molded products and that a release property similar to that of the undivided molded product was retained after division. The present results agree with those in which the releasing rate of the single divided molded product was about half that of the undivided molded product.

The above findings have clarified that since the multi-core press-coated molded product of the present invention is easy to divide and its drug release is controlled irrespectively of whether the molded product is divided, it is possible in the present invention to readily manufacture a molded product whose cores remain completely covered by the outer layer even after division.

While detailed descriptions have been given of the method of manufacturing the multi-core press-coated molded product of the present invention, the apparatus therefore, and the multi-core press-coated molded product resulting therefrom, the technical scope of the present invention is not limited to the aforementioned embodiments.

It is possible in the present invention to mold a multi-core press-coated molded product in a single step from powder or granular particles without supplying cores that are molded products manufactured in advance. This not only ensures high production efficiency and avoids various core-related problems but also allows for a plurality of cores to be arranged at specific positions, reducing to the minimal possible level variations between finished molded products, and thereby allowing for manufacture of highly accurate quality-assured molded products. Therefore, the present invention makes multi-core press-coated molded products industrially viable in various fields and is best suited notably to the field of pharmaceutical drugs where accuracy is essential for molded products.

What is claimed is:

1. A method of manufacturing a multi-core press-coated molded product having an outer layer and a plurality of cores, comprising using compression molding means having an upper punch above a die and a lower punch below the die, wherein both the upper punch and the lower punch comprise a center punch having a tip portion split into at least two parts that are separated by a gap and an outer punch that encloses an outer perimeter of the center punch and further has a tip portion that fills the gap at the tip portion of the center punch, with both the center punch and the outer punch being slidable and manipulatable for compression operation; the method comprising:

supply steps of supplying molding material for the outer layer and molding material for the cores respectively to the compression molding means;

a first compression molding step of compression molding the molding material for at least one of the outer layer and the cores in the compression molding means, and a second compression molding step of compression molding the entire molded product including the cores in the compression molding means.

2. The method of manufacturing a multi-core press-coated molded product according to claim 1, comprising:

supplying molding material for the outer layer into spaces defined by the lower outer punch and the lower center punch;

supplying molding material for the cores into spaces defined by the lower outer punch and the molding material for the outer layer supplied in the previous step;

compression molding the molding material for the outer layer and the molding material for the cores to form a molded portion of the outer layer and the cores;

supplying the molding material for the outer layer into a space in the die above and around the molded portion of the outer layer and the cores molded in the previous step; and compression molding the molded portion of the outer layer and the cores and the molding material for the outer layer.

3. The method of manufacturing a multi-core press-coated molded product according to claim 2, further comprising compression molding the molding material for the outer layer to form a molded portion of the outer layer after supplying the molding material for the outer layer.

4. The method of manufacturing a multi-core press-coated molded product according to claim 2, further comprising:

removing residual molding material remaining on the lower outer punch before supplying a next molding material.

5. The method of manufacturing a multi-core press-coated molded product according to claim 3, further comprising:

removing residual molding material remaining on the lower outer punch before supplying the next molding material.

6. The method of manufacturing a multi-core press-coated molded product according to claim 1, comprising:

(a) an outer layer molding step that includes, with the lower center punch being in a lowered position, supplying molding material for the outer layer into outer layer spaces defined by the lower center punch and the lower outer punch, removing excess molding material for the outer layer from the die if such excess molding material is present, and compressing the molding material for the outer layer to form a first molded portion of the outer layer by engaging the upper and the lower center punches;

(b) an outer layer/cores molding step that includes, with the lower center punch being in its lowered position, supplying molding material for cores into core spaces defined by the lower outer punch and the first molded portion of the outer layer, removing excess molding material for the cores from the die if such excess molding material is present, and compressing the molding material for the cores and the first molded portion of the outer layer to form a second molded portion of the outer layer and the cores by engaging the upper and the lower center punches;

(c) a whole molding step that includes, with the lower punch being in its lowered position, supplying molding material for the outer layer into outer layer spaces above and around the molded portion of the outer layer and the cores in the die such that the molded portions of the cores are completely covered by the molding material for the outer layer and the molded portion of the outer layer, removing excess molding material for the outer layer from the die if such excess molding material is present, and compressing the molding material for the outer layer with a second molded portion of the outer layer and the cores to mold the whole of the outer layer and the cores by engaging the upper and the lower punches.

* * * * *